US009132135B2

(12) United States Patent
Albuquerque et al.

(10) Patent No.: US 9,132,135 B2
(45) Date of Patent: *Sep. 15, 2015

(54) METHOD OF TREATING ORGANOPHOSPHOROUS POISONING

(75) Inventors: Edson X. Albuquerque, Baltimore, MD (US); Michael Adler, Bel Air, MD (US); Edna F. R. Pereira, Baltimore, MD (US)

(73) Assignees: UNIVERSITY OF MARYLAND, BALTIMORE, Baltimore, MD (US); THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 1670 days.

This patent is subject to a terminal disclaimer.

(21) Appl. No.: 12/199,250

(22) Filed: Aug. 27, 2008

(65) Prior Publication Data
US 2009/0023706 A1  Jan. 22, 2009

Related U.S. Application Data

(63) Continuation-in-part of application No. 11/575,945, filed as application No. PCT/US2005/033789 on Sep. 23, 2005, now Pat. No. 7,888,346.

(60) Provisional application No. 60/613,121, filed on Sep. 24, 2004.

(51) Int. Cl.
*A01N 43/00* (2006.01)
*A01N 43/46* (2006.01)
*A61K 31/55* (2006.01)
*A61K 31/33* (2006.01)
*A01N 43/08* (2006.01)
*A61K 31/34* (2006.01)
*A61K 45/06* (2006.01)
*A61K 31/46* (2006.01)

(52) U.S. Cl.
CPC .............. *A61K 31/55* (2013.01); *A61K 31/46* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,550,113 A | 10/1985 | Lavretskaya et al. |
| 4,735,953 A | 4/1988 | Lavretskaya et al. |
| 5,480,651 A | 1/1996 | Callaway |
| 5,795,909 A | 8/1998 | Shashoua et al. |
| 5,939,095 A | 8/1999 | Hille et al. |
| 6,114,347 A | 9/2000 | Hille et al. |
| 6,211,230 B1 | 4/2001 | Filbert et al. |
| 6,261,537 B1 | 7/2001 | Klaveness et al. |
| 6,264,917 B1 | 7/2001 | Klaveness et al. |
| 6,331,289 B1 | 12/2001 | Klaveness et al. |
| 6,358,941 B1 | 3/2002 | Snorrason et al. |
| 6,458,812 B1 | 10/2002 | McKittrick et al. |
| 6,576,636 B2 | 6/2003 | Webb et al. |
| 6,589,504 B1 | 7/2003 | Raub et al. |
| 6,602,902 B2 | 8/2003 | Shashoua et al. |
| 6,610,713 B2 | 8/2003 | Tracey |
| 6,617,361 B2 | 9/2003 | Eig |
| 6,670,356 B2 | 12/2003 | Davis |
| 6,680,047 B2 | 1/2004 | Klaveness et al. |
| 6,692,767 B2 | 2/2004 | Burnside et al. |
| 6,716,857 B2 | 4/2004 | Kim et al. |
| 6,720,427 B2 | 4/2004 | Sanner et al. |
| 6,756,385 B2 | 6/2004 | Sanner et al. |
| 6,759,419 B2 | 7/2004 | Kim et al. |
| 6,777,435 B1 | 8/2004 | Momose et al. |
| 6,838,471 B2 | 1/2005 | Tracey |
| 6,858,648 B2 | 2/2005 | Pan et al. |
| 6,900,202 B2 | 5/2005 | Imoto et al. |
| 6,906,081 B2 | 6/2005 | Hey et al. |
| 6,919,330 B2 | 7/2005 | Vaddadi et al. |
| 6,964,957 B2 | 11/2005 | Abreo et al. |
| 6,977,070 B2 | 12/2005 | Dugger, III |
| 7,001,908 B2 | 2/2006 | Godfrey et al. |
| 7,015,345 B2 | 3/2006 | Kawanishi et al. |
| 7,022,725 B2 | 4/2006 | Momose et al. |
| 7,030,081 B2 | 4/2006 | Nistri et al. |
| 7,034,019 B2 | 4/2006 | Kukla et al. |

(Continued)

FOREIGN PATENT DOCUMENTS

| | | |
|---|---|---|
| JP | H09-506360 A | 6/1997 |
| WO | WO 92/20328 | 11/1992 |

(Continued)

OTHER PUBLICATIONS

Dawson et ai., Some adjuncts to Oxime-atropine Therspy for Organophosphate Intoxication: Their Effects on Acetylcholinesterase, Biochemical Pharmacology, 1979, vol. 28 No. 14, pp. 2211-2214.*
Albuquerque, E. et al., Effective countermeasure against poisoning by organophosphorus insecticides and nerve agents, Aug. 29, 2006, PNAS, vol. 103, No. 35, pp. 13220-13225.*
Wilcock, G. et al., Efficacy and safety of galantamine in patients with mild to moderate Alzheimer's disease: multicentre randomised controlled trial, Dec. 9, 2000, BMJ, vol. 321, pp. 1-7.*
Bajgar, J., Prophylaxis against organophosphorus poisoning, Feb. 2004, J. Med. Chem. Def., vol. 1, pp. 1-16.*

(Continued)

*Primary Examiner* — Jason Sims
*Assistant Examiner* — Tori M Strong
(74) *Attorney, Agent, or Firm* — Erickson Kernell Derusseau & Kleypas, LLC

(57) ABSTRACT

The present invention is directed to various methods for treating organophosphorus poisoning in an animal that is at risk of exposure to an organophosphorus compound or preventing organophosphorus poisoning in an animal that has been exposed to an organophosphorus compound, by administering a therapeutically effective amount of galantamine or a salt thereof, or a biologically active analog, derivative, fragment or variant thereof.

20 Claims, 28 Drawing Sheets

(56) References Cited

U.S. PATENT DOCUMENTS

| | | |
|---|---|---|
| 7,034,039 B2 | 4/2006 | Oi et al. |
| 7,038,085 B2 | 5/2006 | Rariy et al. |
| 7,045,527 B2 | 5/2006 | Chen et al. |
| 7,060,270 B2 | 6/2006 | Nicolau et al. |
| 7,078,529 B2 | 7/2006 | Sanner et al. |
| 8,703,762 B2 * | 4/2014 | Albuquerque et al. ....... 514/215 |
| 2005/0013869 A1 | 1/2005 | Chaw et al. |

FOREIGN PATENT DOCUMENTS

| | | |
|---|---|---|
| WO | WO 03/092606 A2 | 11/2003 |
| WO | 2008/022365 A2 | 2/2008 |

OTHER PUBLICATIONS

Albuquerque, et al., Effective countermeasure against poisoning by organophosphorus insecticides and nerve agents, 2006, PNAS, vol. 103, No. 35, pp. 13220-13225.*

Wilcock, et al., Efficacy and safety of galantamine in patients with mild to moderate Alzheimer's disease: multicentre randomised controlled trial, 2000, BMJ, vol. 321, pp. 1-7.*

Bajgar, J., Prophylaxis against organophosphorus poisoning, 2004, J. Med. Chem. Def., vol. 1, pp. 1-16.*

Wilcock et al., Efficacy and safety of galantamine in patients with mild to moderate Alzheimer's disease: multicentre randomised controlled trial, 2000, BMJ, vol. 321, pp. 1-7.*

Albuquerque et al., Effective countermeasure against poisoning by organophosphorus insecticides and nerve agents, 2006, PNAS, vol. 103, No. 35, pp. 13220-13225.*

Australian Office Action for corresponding AU Application No. 2005289808, May 27, 2010.

International Search Report and Written Opinion dated Dec. 28, 2006 for corresponding International PCT App. No. PCT/US05/33789.

Dawson et al., Some adjuncts to oxime-atropine therapy for organophosphate intoxication—Their effects on acetylcholinesterase, journal, 1979, vol. 28 No. 9, pp. 2211-2214, Biochemical Pharmacology, United States.

European Office Action dated Mar. 19, 2009 for corresponding European Patent App. No. 05 812 994.1.

Kugusheva, L. I. et al., Interaction of Membrane-Bound and Solubilized Acetylcholinesterase of Human and Bovine Erythrocytes with Organophosphorus Inhibitors, journal, 1986, vol. 58 No. 3, pp. 13-18, Ukrainskii Biokhimicheskii Zhurnal, Russia.

Leaning et al., Bloody Sunday Report of a Medical Mission to Soviet Georgia, 1990, Physicians for Human Rights, pp. 1-82.

Muggleton et al., Assessmnet of a Combination of Physostigmine and Scopolamine as Pretreatment Against the Behavioural Effects of Organophosphates in the Common Marmoset, journal, 2003, vol. 166 No. 3, pp. 212-220, Physchopharmacology, Springer-Verlag, Germany.

Samochocki et al., Galantamine is an Allosterically Potentiating Ligand of Neuronal Nicotinic but Not of Muscarinic Acetylocholine Receptors, journal, 2003, vol. 305 No. 3, pp. 1024-1036, The Journal of Pharmacology and Experimental Therapeutics, United States.

Santos et al., Low Concentrations of Pyridostigmine Prevent Soman-Induced Inhibitions of GABAergic Transmission in the Central Nervous System: Involvement of Muscarinic Receptors, journal, 2003, vol. 304 No. 1, pp. 254-265, The Journal of Pharmacology and Experimental Therapeutics, United States.

Santos et al., Spine Density and Dendritic Branching Pattern of Hippocampal CA1 Pyramidal Neurons in Neonatal Rats Chronically Exposed to the Organophosphate Paraoxon, journal, 2004, vol. 25, pp. 481-494, NeuroToxicology, Elsevier, United States.

Santos et al., The Nicotinic Allosteric Potentiating Ligang Galanthamine Facilitates Synaptic Transmission in the Mammalian Central Nervous System, journal, 2002, vol. 61 No. 5, pp. 1222-1234, Molecular Pharmacology, The American Society for Pharmacology and Experimental Therapeutics, United States.

Shabunova et al., Effects of cholinesterase inhibitors on the electrical excitability of the membrane of frog muscle fiber, journal, 1982, vol. 68 No. 9, pp. 1223-1228, Fiziol Zh SSSR Im I M Sechenova, Russia (Abstract).

Storch et al., Physostigmine, galanthamine and codeine act as 'non-competitive nicotinic receptor agonists', on clonal rat pheochromoctyoma cells, journal, 1995, vol. 290 No. 3, pp. 207-219, European Journal of Pharmacology, Elsevier Science B.V., Netherlands.

Tonkopii et al., Study of Characteristics of the Interaction of Galanthamine with Acetyl Cholin Esterase of the Mouse Brain in In-Vivo Experiments, 1976, vol. 82 No. 7, pp. 823-825.

Tonkopii V. D., Oxidative stress in the mechanism of organophosphates neurotoxicity, 2003, vol. 144 No. Suppl. 1, pp. 132.

Albuquerque et al., Effective countermeasure against poisoning by organophosphorous insecticides and nerve agents, PNAS Aug. 29, 2006; vol. 103 No. 35; pp. 13220-13225.

Kenneth J. Kellar, Overcoming Inhibitions, PNAS Sep. 5, 2006; vol. 103 No. 36; pp. 13263-13264.

Response to the Communication pursuant to Rule 161(2) and 162 EPC in corresponding European Patent Application No. 09 810 587. 7, May 26, 2011.

Bajgar Jiri: Organophosphates/nerve agent poisoning: mechanism of action, diagnosis, prophylaxis, and treatment, Advances in Clinical Chemistry, Academic Press, London, GB, vol. 28. Jan. 1, 2004, pp. 151-216, XPOO91 09278, ISSN: 0065-2423. DOI: 10.1016/S0065-2423(04)38006-6.

Lopes et al.: "Competitive Antagonism between the Nicotinic Allosteric Potentiating Ligand Galantamine and Kynurenic Acid at α7 Nicotinic Receptors", Journal of Pharmacology and Experimental Therapeutist, Published online before print Apr. 19, 2007, doi: 10.. 1124/jpet.107.123109 JPET Jul. 2997 vol. 322 No. 1 48-58.

Ludwig et al.: "Localization by site-directed mutagenesis of a galantamine binding site on a7 nicotinic acetylcholine receptor extracellular domain", Journal of Receptors and Signal Transduction, 2010; 30(6): 469-483.

Mamczarz et al."Galantamine counteracts development of learning impairment in guinea pigs exposed to the organophosphorus poison soman: Clinical significance", NeuroToxicology 32 (2011), pp. 785-798.

Pereira et al.,"Unconventional Ligands and Modulators of Nicotinic Receptors", Wiley Periodicals Inc. 2002, pp. 479-500.

Samochocki et al: "Galantamine is an allosterically potentiating ligand of the human α4/β2 nAChR", Acta Neurologica Scandinavica 2000: Supplement 176: pp. 68-73.

Romano Jr. et al: "Novel Medical Countermeasures for Organophosphorous Intoxication: Connection to Alzheimer's Disease and Dementia"—Chemical Warfare Agents: Chemistry, Pharmacology, Toxicology, and Therapeutics, 2nd Ed., 2008, p. 219-229.

Extended European Search Report in corresponding European Patent Application No. 09 810 587.7, dated Mar. 21, 2014.

* cited by examiner

A, B and C

D and E

AN ACUTE EXPOSURE TO SOMAN LEADS TO BRAIN ATROPHY

PRE-SOMAN EXPOSURE    POST-SOMAN EXPOSURE

FIG. 7
HISTOLOGICAL CONFIRMATION OF THE BRAIN DAMAGE OBSERVED IN THE MRI OF SOMAN-EXPOSED GUINEA PIG BRAIN
CONTROL
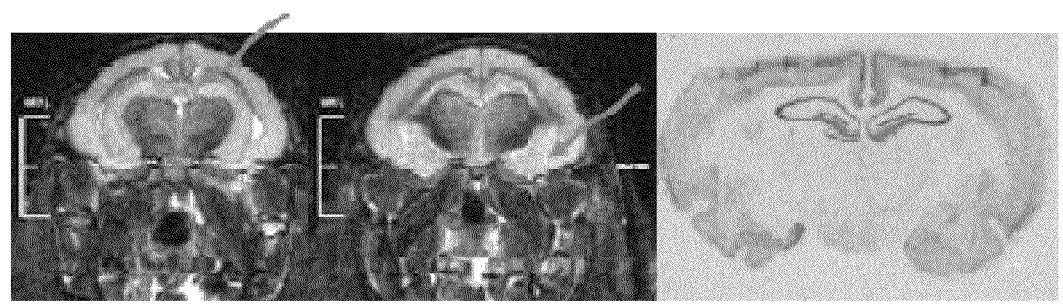
7 HOURS POST-SOMAN EXPOSURE HISTOLOGICAL CONFIRMATION OF THE BRAIN DAMAGE OBSERVED
IN THE MRI OF SOMAN-EXPOSED GUINEA PIG BRAIN

FIG. 9

EFFICACY OF GALANTAMINE IN PREVENTING BRAIN DAMAGE INDUCED BY ACUTE EXPOSURE TO 1.25X LD50 SOMAN. A VOXL-BASED MORPHOMETRIC ANALYSIS

FIG. 11 A-B
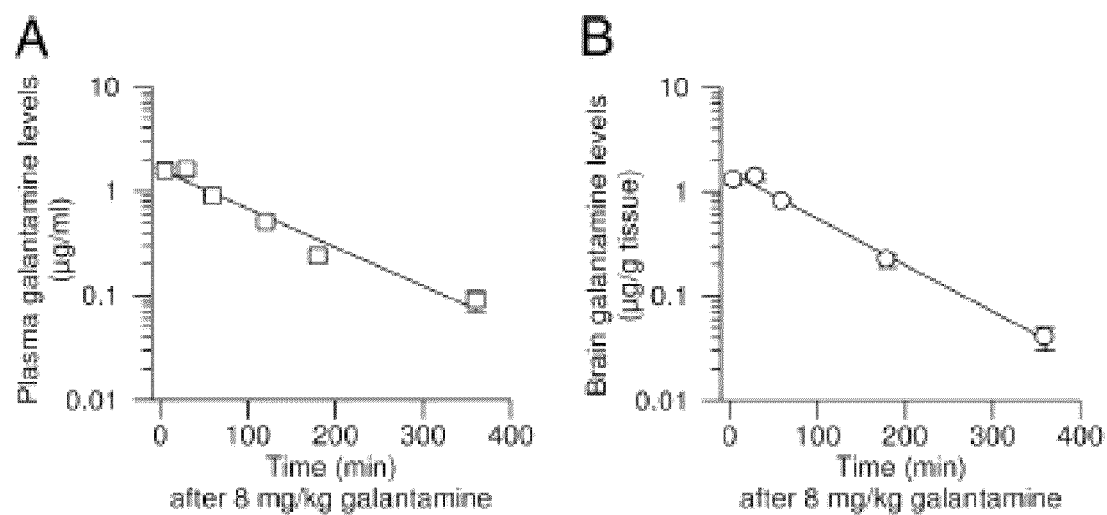

FIG. 11 C-D
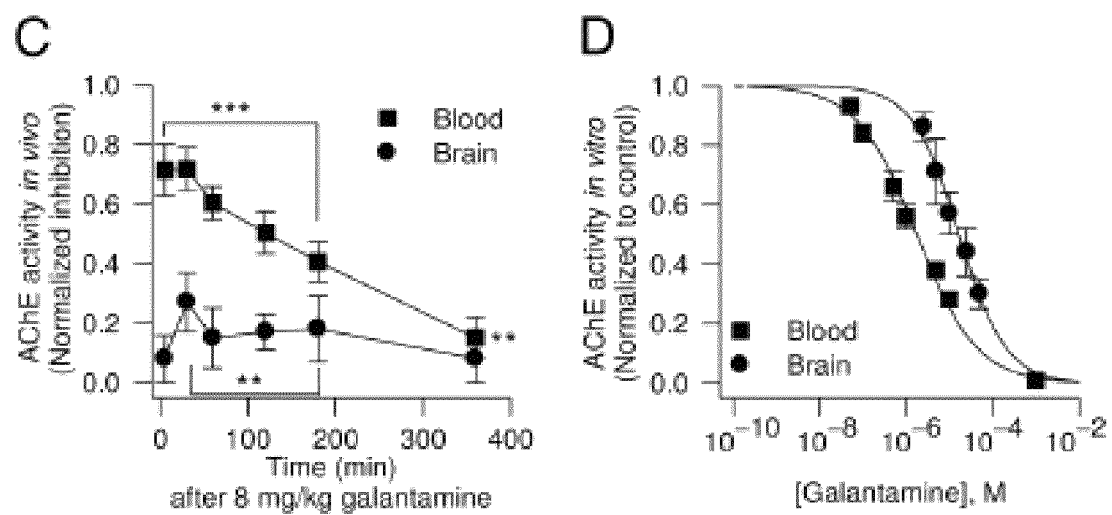

Effectiveness of donepezil as pre-treatment to prevent the lethality of 1.5xLD50 soman in guinea pigs Effectiveness of donepezil as a post-treatment against the lethality of 1.0xLD50 soman in guinea pigs Effectiveness of rivastigmine as pre-treatment to prevent the lethality of 1.5xLD50 soman in guinea pigs Effectiveness of rivastigmine as a post-treatment against the lethality of 1.0xLD50 soman in guinea pigs Toxicity of doses of (±)huperzine-A that are effective as pre-treatment against the lethality of 1.5xLD50 soman in gu (±)Huperzine-A administered after a sub-lethal dose of soman triggered signs of acute toxicity and decreased survival of the anim

METHOD OF TREATING ORGANOPHOSPHOROUS POISONING

CROSS-REFERENCE TO RELATED APPLICATIONS

This application is a continuation-in-part of U.S. application Ser. No. 11/575,945, filed on Mar. 23, 2007, under 35 U.S.C. §120, which claims the benefit of U.S. Provisional Patent Application No. 60/613,121 filed Sep. 24, 2004, under 35 U.S.C. §119(e). The entire contents of these applications are hereby incorporated by reference as if fully set forth herein.

STATEMENT OF GOVERNMENT SUPPORT

The invention described herein was made, at least in part, with funding from the U.S. Army under Grant No. DAAD19-02-D-001, NINDS/NIH U01NS059344-02, ARO contract W911NF-06-1-0098. Therefore, the government has certain rights in the invention.

TECHNICAL FIELD OF THE INVENTION

The present invention relates to a method of treating organophosphorus poisoning.

BACKGROUND OF THE INVENTION

Organophosphorus compound is (OP) are a common class of chemicals used as pesticides, herbicides, and nerve agents The nerve agents soman (3-(Fluoro-methyl-phosphoryl)oxy-2,2-dimethyl-butane), sarin (2-(Fluoro-methylphosphoryl)oxypropane), VX (S-2-[diisopropylamino]O— ethyl methylphosphonothioate), tabun (ethyl N,N-dimethylphosphoramidocyanidate) and Novichok agents are among the most lethal weapons of mass destruction ever developed. Some of these nerve agents were used with catastrophic results in wars and also in terrorist attacks in Japan in the 1990s. The majority of pesticides are also OPs (such as parathion, fenthion, malathion, diazinon, dursban, chlorpyrifos, terbufos, acephate, phorate, methyl parathion, phosmet, azinphos-methyl, and dimethoate), and intoxication with these compounds represents a major public-health concern worldwide. Chlorpyrifos, the organophosphate agent of dursban, is found in some popular household roach and ant sprays, including Raid™ and Black Flag™.

Due to their physical state and high lipophilicity, OPs rapidly penetrate and accumulate in the central nervous system (CNS). OP poisoning of military personnel on the battlefield and of common citizens in the event of a terrorist attack with nerve agents has caused an increase in concern for public and governmental authorities around the world in recent years. In addition, increased demand for food and ornamental crops has resulted in an increase in the use of toxic OP-based pesticides, including parathion and malathion, in developed and developing countries, which has resulted in an increase in the accidental poisoning of farmers and gardeners. The possibility of further terrorist attacks with nerve agents and the escalating use of OP pesticides underscore the urgent need to develop effective and safe antidotes against OP poisoning.

Although different OPs interact with specific targets in the peripheral and central nervous systems, signs and symptoms of acute intoxication with high doses of nerve agents or OP pesticides appear to result in part from their common action as irreversible inhibitors of acetylcholinesterase (AChE), the enzyme that catalyzes the inactivation of the neurotransmitter acetylcholine (Bajgar, J. (2004) *Adv. Clin. Chem.* 38, 151-216). In the periphery, acetylcholine accumulation leads to persistent muscarinic receptor stimulation that triggers a syndrome whose symptoms include miosis, profuse secretions, bradycardia, bronchoconstriction, hypotension, and diarrhea. OP poisoning also leads to overstimulation followed by desensitization of nicotinic receptors, causing severe skeletal muscle fasciculations and subsequent weakness. Central nervous system-related effects include anxiety, restlessness, confusion, ataxia, tremors, seizures, cardiorespiratory paralysis, and coma.

OPs are also known to cause an Intermediate Syndrome (IMS), which results in muscle weakness in the limbs, neck, and throat that develops in some patients 24-96 hours after poisoning; long-term nerve damage sometimes develops 2-3 weeks after poisoning. Researchers from Sri Lanka, Australia, and the UK recently showed that changes in neuromuscular transmission patterns often occur before a physician can make an IMS diagnosis from clinical signs. About 38% of patients studied presented with muscle weakness that was not severe enough for an IMS diagnosis. Thus, IMS is a spectrum disorder. At one end of the spectrum the patients demonstrate only the electrophysiological abnormalities without clinically detectable muscle weakness, and at the other end, patients progress to severe muscular weakness with deterioration of electrophysiological measurements and the risk of respiratory failure.

None of the current therapies for treating or preventing OP poisoning and IMS have been ideal. Therefore, there is still a critical need for an effective and safe method of treating or preventing OP poisoning. This and other objects and advantages, as well as additional inventive features, will become apparent from the detailed description provided herein.

DEFINITIONS

Unless otherwise indicated, a "therapeutically effective amount" of galantamine is an amount that provides a therapeutic benefit in the prevention, treatment or management of OP poisoning (organophosphorus poisoning), delays or minimizes one or more symptoms associated with it, or enhances the therapeutic efficacy of another therapeutic agent. An agent is said to be administered in a "therapeutically effective amount" if the amount administered results in a desired change in the physiology of a recipient mammal, (e.g. prevents or decreases one or more symptoms of organophosphorus poisoning).

Toxic dose/amount means any amount that causes an adverse effect in the victim.

Lethal dose/amount of an OP compound means a dose of more than about $0.8 \times LD_{50}$.

Sublethal dose/amount of an OP compound means a dose of less than about $0.8 \times LD_{50}$.

A subject at risk of developing OP poisoning means a subject that has been exposed to or is at risk of being exposed to a toxic level of OP.

By preventing OP poisoning is meant that a therapeutic regimen is administered to prevent OP poisoning in an animal that may or may not have been exposed to OP, but is asymptomatic or has no biochemical indicia of OP exposure.

By treating OP poisoning is meant that a therapeutic regimen is administered to treat OP poisoning in an animal that has been exposed to a toxic amount of OP and that has physiologic signs or shows a biochemical change indicative of OP poisoning. Treatment minimizes or counteracts one or more signs or biochemical changes associated with OP poisoning.

Galantamine" means galantamine (287.4 molecular weight) and all biologically active salts, analogs, fragments, derivatives and variants or chemically modified forms thereof, as well as chemically synthesized, recombinant, and naturally-occurring isolated and purified forms. Variants include esters, amides, prodrugs, metabolites, enantiomers, polymorphs, analogs, etc. that induce a desired pharmacological or physiological effect. Certain galantamine analogs and derivatives that can be used in the present invention are described in Davis et al., U.S. Pat. No. 6,150,354, Davis et al.; U.S. Pat. No. 6,319,919; and Davis et al., U.S. Pat. No. 6,670,356, which patents are incorporated in their entirety as if fully set forth herein, except where terminology is not consistent with the definitions herein. A number of galantamine analogs occur naturally or have been isolated from natural products (The Alkaloids, R. H. F. Manske editors, Academic Press, N.Y., 15th edition). "Galantamine" includes any pharmaceutically acceptable preparation including controlled release formulations as described in Gore et al., U.S. Application No. US 2007/0092568, incorporated herein by reference.

BRIEF DESCRIPTION OF THE DRAWINGS

FIG. 7 Histological confirmation of brain damage caused by acute exposure to $1.25 \times LD_{50}$.

FIG. 9 Vox L-based morphometric contrast maps showing that 8 mg galantamine administered 30 minutes before acute exposure to $1.25 \times LD_{50}$ protects against brain damage. Images obtained at 7 hours after the soman challenged are contrasted with those obtained before the treatment. Only those voxels that reached a significance level of p<0.05 are shown.

FIG. 11 Differential sensitivity of brain and blood AChE activities to inhibition by galantamine in vivo and in vitro. A. Logarithm of the concentrations of galantamine measured in blood and brain samples obtained at various times after treatment of guinea pigs (n=4-6 animals/time point) with galantamine (8 mg/kg, i.m.) is plotted against time. B, left graph. AChE activity measured in samples from saline-treated animals was taken as 1 and used to normalize activity the activity measured in samples obtained at various times after treatment of animals with galantamine (8 mg/kg, i.m.). Normalized inhibition (1—normalized activity) was plotted against the time at which samples were obtained (left graph). Asterisks indicate that results from galantamine- and saline-treated animals are significantly different at p<0.001 (*) or p<0.01 () (ANOVA followed by Dunnett post-hoc test). B, right graph. Increasing concentrations of galantamine were added in vitro to brain homogenates and blood samples obtained from naive animals. AChE activity in untreated samples was taken as 1 and used to normalize activity measured in galantamine-treated samples. The graph of normalized AChE activity vs. galantamine concentrations was fitted with the Hill equation. Results are presented as mean and SEM (n=4-6 animals/galantamine concentration).

SUMMARY OF THE INVENTION

Figure 1:
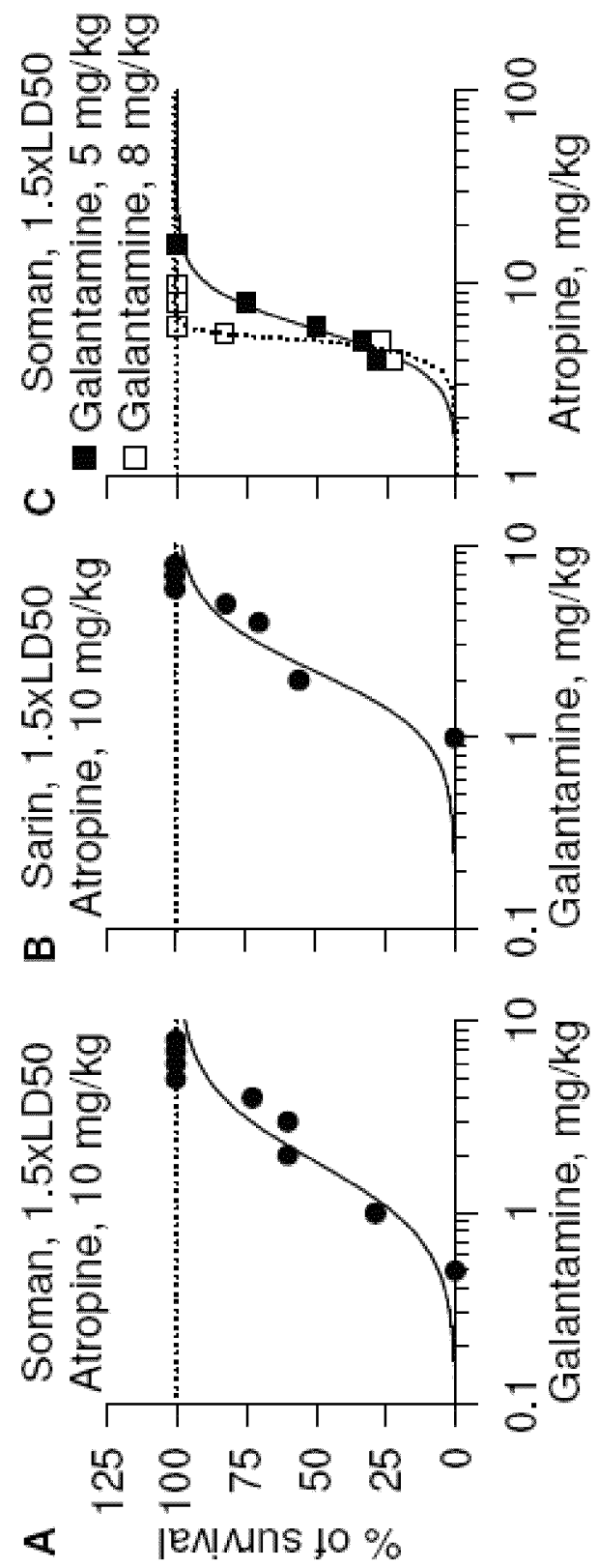
FIG. 1 Pretreatment with galantamine prevents the acute toxicity of lethal doses of OPs: Comparison with pyridostigmine and huperzine. In all experiments, guinea pigs received an i.m. injection of selected doses of galantamine, pyridostigmine, or huperzine followed 30 minutes later by a single s.c. injection of $1.5 \times LD_{50}$ (42 μg/kg) or $2.0\_LD_{50}$ (56 μg/kg) soman, $1.5 \times LD_{50}$ sarin (56 μg/kg), or the indicated doses of paraoxon. At 1 minute after the OP challenge, all animals received atropine (1-10 mg/kg, i.m.). (A-C) Dose-response relationships for galantamine or atropine to maintain 24 hour survival of animals challenged with nerve agents. (D) Dose-response relationship for paraoxon induced decrease in 24 hour survival of atropine-treated guinea pigs that were pretreated with saline or galantamine. (E) Effects of increasing doses of pyridostigmine or huperzine in maintaining 24 hour survival of soman challenged, atropine-treated animals. Each group had 8-12 animals. Percent survival represents the percent of animals that were kept alive because they presented no life-threatening symptoms.
Figure 1:
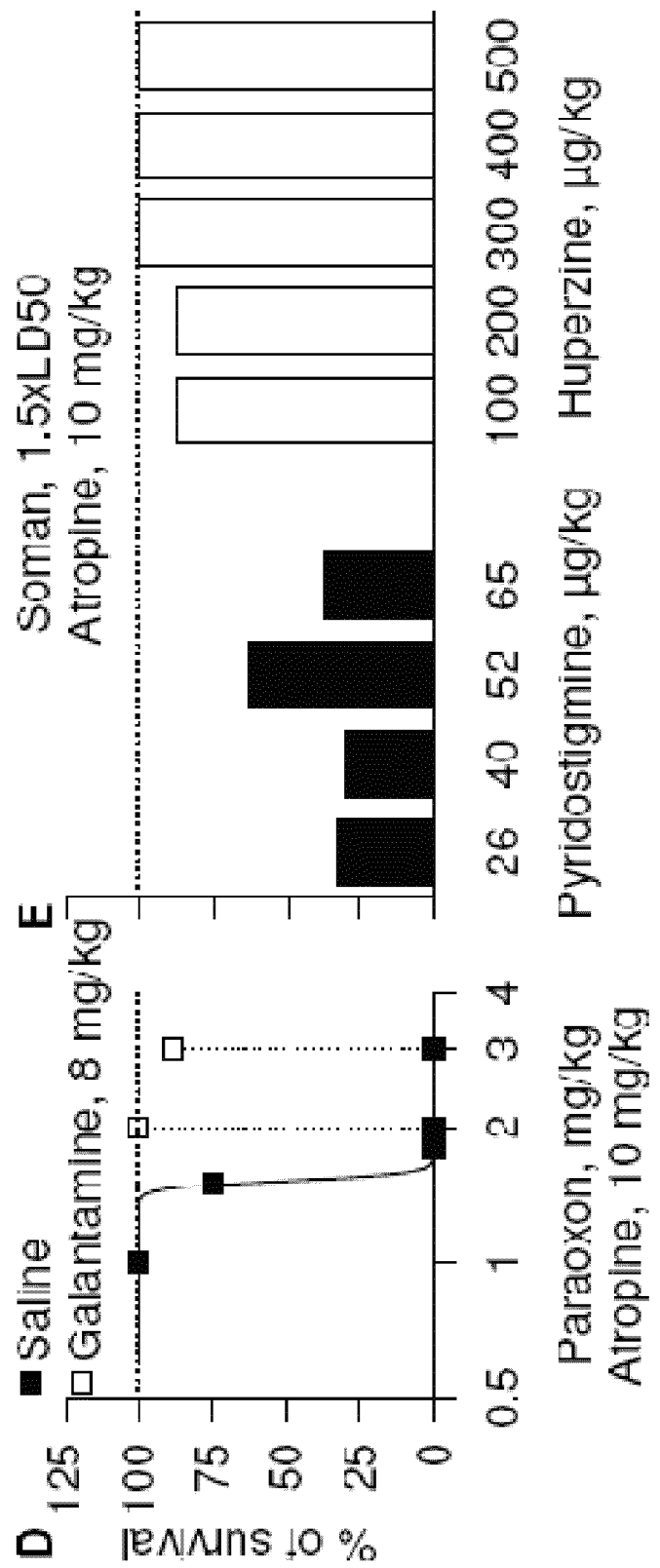

Certain embodiments of the invention are directed to various methods for treating organophosphorus poisoning in an animal that is at risk of exposure to an organophosphorus compound or preventing organophosphorus poisoning in an animal that has been exposed to an organophosphorus compound, by administering a therapeutically effective amount of galantamine or a salt thereof, or a biologically active analog, derivative, fragment or variant thereof. The therapeutically effective dose is typically from about 3 to about 12 mg. In a preferred embodiment, galantamine is administered by intramuscular injection, subcutaneous injection, intranasal or oral administration.

In an embodiment, the animal has been exposed to a lethal dose of the organophosphorus compound in an amount of ≥ about $0.8 \times LD_{50}$, and galantamine is administered in a range from about 5 hours before until about 30 minutes after exposure to the lethal dose of the OP, or from about 1 hour before until about 15 minutes after exposure to the lethal dose of the OP. In one embodiment where the lethal dose is ≥ about 1.5 $LD_{50}$, the method includes the further steps of administering a therapeutically effective amount of a muscarinic receptor antagonist or a salt thereof or a biologically active analog, derivative, fragment or variant thereof after exposure to the lethal dose of the OP, preferably atropine in an amount of from about 1 mg to about 12 mg. In another preferred embodiment, galantamine is administered together with atropine after exposure to the lethal dose of ≥ about 1.5 $LD_{50}$. In another preferred embodiment, the therapy for exposure to the lethal dose of ≥ about 1.5 $LD_{50}$ further includes administering additional doses of atropine about every 3 to 5 minutes after the first administration of atropine as long as there are symptoms of OP poisoning, preferably in an amount of from about 1 to about 10 mg, and more preferably about 2 mg.

In some embodiments, the OP is a nerve agent including but not limited to soman, sarin, and VX, tabun, and Novichok agents. When the exposure is to a lethal dose of ≥ about 1.5 $LD_{50}$ of a nerve agent, galantamine is preferably administered in an amount of from about 6 to about 10 mg. When the exposure is to a lethal dose of ≥ about 1.5 $LD_{50}$ of a pesticide including parathion, fenthion, malathion, diazinon, dursban, chlorpyrifos, terbufos, acephate, phorate, methyl parathion, phosmet, azinphos-methyl, and dimethoate, galantamine is preferably administered in an amount from about 6 to about 12 mg.

In a preferred embodiment for treating exposure to lethal doses of ≥ about 1.5 $LD_{50}$ of either a nerve agent or an pesticide or both, additional doses of galantamine are administered up to about three times per day for up to about a month after the exposure. These additional doses of galantamine are typically administered in an amount from about 3 to about 6 mg.

In some embodiments, the animal has been exposed to a sublethal dose of the organophosphorus compound in an amount of less than about $0.8 \times LD_{50}$ global. In a preferred embodiment for treating or preventing OP poisoning after exposure to the sublethal dose of the organophosphorus compound, galantamine is administered in an amount from about 3 to about 10 mg. In a preferred embodiment, additional doses of galantamine are administered up to about three times per day for up to about 3 days after the sublethal exposure, preferably in an amount of about 3 to about 6 mg. Galantamine alone is sufficient for treating or preventing OP poisoning where the amount of OP is about $1 \times LD_{50}$ or lower; an antimuscarinic agent is not required.

Another embodiment is directed to a method for preventing organophosphorus poisoning in an animal that is at risk of repeated exposure to sublethal doses of an organophosphorus compound, by administering a therapeutically effective amount of galantamine or a salt thereof, or a biologically active analog, derivative, fragment or variant thereof up to three times per day for a duration of the risk. In a preferred embodiment, galantamine is administered in an amount from about 3 to about 6 mg.

In another embodiment, OP poisoning is treated or prevented by administering a therapeutic amount of galantamine either before or after exposure, in an amount that maintains plasma galantamine levels at about 2 to about 3 micromolar for up to a month after the exposure.

Another embodiment is directed to a pharmaceutical composition that includes galantamine or a salt thereof, or a biologically active analog, derivative, fragment or variant thereof and a muscarinic receptor antagonist, preferably, atropine or a salt thereof, or a biologically active analog, derivative, fragment or variant thereof. In a preferred embodiment of the composition, galantamine is in an amount from about 3 to about 12 mg per unit, and atropine is in an amount about 1 to about 12 mg per unit.

Another embodiment is directed to a method of treating or preventing the loss of cognitive function or neuronal degeneration in an animal after organophosphorus poisoning by administering a therapeutically effective amount of galantamine or a salt thereof, or a biologically active analog, derivative, fragment or variant thereof, preferably in an amount from about 3 to about 10 mg up to three times per day as long as symptoms of OP poisoning persist, and optionally also up to three times per day after symptoms of OP poisoning have disappeared, preferably in an amount of from about 3 to about 6 mg.

Another embodiment is directed to a method of treating or preventing intermediate syndrome in an animal that is at risk of developing it by administering a therapeutically effective amount of galantamine or a salt thereof, or a biologically active analog, derivative, fragment or variant thereof preferably in an amount from about 3 to about 10 mg, administered up to three times per day after exposure for up to a month after exposure.

DETAILED DESCRIPTION OF THE INVENTION

We have discovered that therapeutically effective amounts of galantamine, a competitive, reversible and weak acetylcholinesterase (AChE) inhibitor, can be administered to an animal, preferably a human subject, that has been exposed to or that is at risk of exposure to lethal or sublethal doses of OP to treat or prevent OP poisoning. Galantamine alone is an effective antidote for treating or preventing OP poisoning when administered up to about 3 hours after exposure to doses of OPs of about $1.0 \times LD_{50}$ or lower. However, if exposure is to higher doses of OPs (about 1.5×LD 50 or higher), then in addition to galantamine administration before or after OP exposure, the victim requires further treatment as soon after exposure as possible with atropine or other muscarinic receptor antagonist. These and other embodiments of the invention are described in more detail below and in the Examples that follow. The amount of galantamine and the timing of administration vary depending on the amount of OP exposure.

Current Strategies for Treating OP Poisoning

Current therapeutic strategies to decrease OP toxicity include administering atropine to reduce the muscarinic syndrome, oximes to reactivate OP-inhibited AChE, and benzodiazepines to control OP-triggered seizures (Bajgar, J. (2004) *Adv. Clin. Chem.* 38, 151-216). Atropine acts by blocking the action of acetylcholine at muscarinic receptors. Troops who are likely to be attacked with chemical weapons often carry autoinjectors with atropine and oximes (reversible acetylcholinesterase (AChE) inhibitors. which can be quickly injected into the thigh). Atropine is often used in conjunction with pralidoxime chloride. Atropine is given as an antidote to SLUDGE (Salivation, Lacrimation, Urination, Diaphoresis, Gastrointestinal motility, Emesis) symptoms caused by organophosphate poisoning. The limitations of these treatments are well recognized (Buckley, N. A., et al., (2004) *J. Toxicol. Clin. Toxicol.* 42, 113-116), and alternative therapies have been sought. Among these therapies are the use of phosphotriesterases and butyrylcholinesterase (BuChE) enzymes that act as OP scavengers (Doctor, B. P., ET AL., and (1991) *Neurosci. Biobehav. Rev.* 15, 123-128; Ghanem, E. & Raushel, F. M. (2005) *Toxicol. Appl. Pharmacol.* 207, 459-470). However, potential adverse immunological reactions and the difficulty in delivering these large molecules are problematic. Pyridostigmine bromide, a quaternary carbamate that reversibly inhibits AChE and BuChE with similar potencies and does not cross the blood-brain barrier appreciably, has been approved for use among military personnel who are under threat of exposure to nerve agents. Pretreatment with pyridostigmine prevents OP-induced irreversible AChE inhibition in the periphery, and it increases survival of animals acutely exposed to lethal doses of nerve agents, provided that atropine and oximes are administered promptly after an OP exposure (Bajgar supra, Wetherell, J., et al. (2002) *Neurotoxicology* 23, 341-349, and Leadbeater, L. et al. (1985) *Fundam. Appl. Toxicol.* 5, S225-S231).

When used acutely before an OP exposure, reversible AChE inhibitors that are capable of crossing the blood-brain barrier, including physostigmine, tacrine, and huperzine A (hereafter referred to as huperzine), afford better protection than pyridostigmine against OP toxicity, but generally this protection occurs at doses that produce significant incapacitation and central nervous system impairment. (Deshpande, S. S., et al., (1986) *Fundam. Appl. Toxicol.* 6, 566-577, Grunwald, J., et al. (1994) *Life Sci.* 54, 991-997, Fricke, R. F., et al. (1994) *Drug Chem. Toxicol.* 17, 15-34, Lallement, G., et al. (2002) *Neurotoxicology* 23, 1-5).

The use of carbamic acid esters to treat OP poisoning has been tried. However, they have a low therapeutic index. (Leadbeater, L. Chem. in Brit. 24, 683, 1988; Fleischer, J. H., et al. Biochem. Pharmacol. 14, 641, 1965, and Berry, W. K., Davies, D. R. Biochem. Pharmacol, 19, 927, 1970). An increased protective action can be achieved by administering the drug physostigmine, however, the effective doses of physostigmine are known to cause cognitive deficits (Myhrer et al., Eur J. Pharmacol. 483:271-279, 2004).

Hille, et al. (U.S. Pat. No. 6,114,347) describe a prophylactic treatment for OP poisoning by administering a combination drug before exposure that includes (a) at least one acetylcholinesterase inhibitor (an indirect parasympathomimetic agent) to protect against organophosphorus cholinesterase inhibitors, and at least one parasympatholytic agent, meaning substances having an affinity for muscarinic acetylcholine receptors without causing an adverse effect, such as atropine. Hille mentions that galantamine can be used in the combination drug. The Hille therapy requires that the subject be treated before exposure to the OP and that the acetylcholinesterase inhibitor be administered together with the parasympathomimetic in a single drug. By contrast, we have discovered that galantamine can be administered alone either before or after exposure to OPs, and that atropine is only necessary for very highly lethal levels of OP exposure above about $1.5 \times LD_{50}$ or higher, and even then it is administered after, not before, exposure.

Galantamine Structure and Function

Galantamine (i) is a reversible acetylcholinesterase inhibitor that crosses the blood-brain barrier (Corey-Bloom, J. (2003) *Int. J. Clin. Pract.* 57, 219-223); (ii) has anticonvulsant properties (Dreyer, R. (1968) Munch. Med. Wochenschr. 110, 1481; Losev, N. A. & Tkachenko, E. I. (1986) Biull. Eksp. Biol. Med. 101, 436-438); and (iii) prevents neurodegeneration, which is a hallmark of OP poisoning (Pereira, E. F. R., Hilmas, C., Santos, M. D., Alkondon, M., Maelicke, A. & Albuquerque, E. X. (2002) J. Neurobiol. 53, 479-500; Arias, E., et al. (2004) Neuropharmacology 46, 103-114; Kihara, T., et al. (2004) Biochem. Biophys. Res. Commun. 325, 976-98217-19; Shih, T. M., et al. (2003) Toxicol. Appl. Pharmacol. 188, 69-8020). The experiments described herein used guinea pigs, the best nonprimate model to predict the effectiveness of antidotal therapies for OP poisoning in humans (Maxwell, D. M., et al., Exp. Ther. 246, 986-991. Because of their low levels of circulating carboxylesterases, guinea pigs, like nonhuman primates, are very sensitive to OPs, and they respond more like primates than do rats or mice to antidotal therapies (Maxwell supra).

Medicinal use of galantamine is described in Horner's classic epic *The Odyssey*. In the 1950's a Russian scientist discovered that it reverses tubocurare-induced anesthesia. Researchers became interested in the compound as an Alzheimer's drug in the late 1980's. Galantamine was approved for the indication of mild to moderate dementia of the Alzheimer's type in 2001 and now has regulatory approval for this indication in at least 29 countries.

Galantamine and its salts have been employed as a pharmaceutically active agent for long term administration in the treatment of a variety of disorders including mania, alcoholism, nicotine dependence, and Alzheimer's disease. In particular, galantamine hydrobromide is used for the treatment of Alzheimer's disease and is currently formulated in film-coated tablets of 4 milligrams (mg), 8 mg and 12 mg doses for daily oral administration under the trade name REMINYL [Razadyne] (Janssen-Cilag, Ltd., UK). Galantamine has also been administered for treating arthritis and rheumatoid disorders in amounts up to 30 mg/day including administration in 5-10 mg amounts multiple times per day. Galantamine can be administered over extended periods of time, even over a period of years, because of its low toxicity and relatively rapid clearance even over years. Galantamine is commercially available under the trade names Razadyne™, Razadyne ER™, Reminyl™, Nivalin™, and Memeron™.

Galantamine is a tertiary alkaloid which has been isolated from the bulbs of the Caucasian snowdrop, Galanthus woronowi (Proskurnina, N. F. and Yakoleva, A. P. (1952), (In Russian). Zh. Obschchei Khim. (J. Gen. Chem.) 22, 1899-1902; Chem. Abs. 47,6959, 1953). It has also been isolated from the common snowdrop Galanthus Nivalis.

Because galantamine is able to pass through the blood-brain barrier (BBB), it has pharmacologic activity both peripherally and in the central nervous system. Galantamine also functions as an allosteric potentiating ligand (APL) of nicotinic acetylcholine receptors (nAChRs), and is able to "rescue" some nicotinic receptors from desensitization by OP exposure (reviewed in Pereira et al., J Neurobiol 53:479-500, 2002; Samochocki, M., et al., J. Pharmacol Exp Ther 305, 1024-1036). This property is important in the context of OP poisoning because an excessive amount of acetylcholine induces massive desensitization of nicotininc acetylcholine receptors.

The elimination half-life of galantamine hydrobromide is over four hours, and it has practically complete renal elimination. A complete elimination of metabolites of galantamine takes place in about 72 hours. (Snorrason, E., et al. U.S. Pat. No. 6,358,941). Others have described metabolic pathways and renal excretion in the elimination of galantamine (see e.g., G. Mannens, et al (2002) Drug Metabolism and Disposition, 30:553-563).

The side effects of galantamine are either nausea or vomiting and headache, however, these are uncommon especially if medication is gradually increased over time to the optimal active dose. Of course, this cannot be done in a crisis of organophosphorus poisoning such as a terrorist attack, but these adverse effects are far outweighed by the benefits. Galantamine also has the desired property of being about 50 times more selective for acetylcholinesterase than butyrylcholinesterase, an acetylcholinesterase scavenger. (Thomsen and Kewitz, Life Sciences, 46, 1553-1558, 1990). This means that in contrast to other non-selective cholinesterase inhibitors, including physostigmine and pyridostgimine, galantamine can protect AChE from OP-induced irreversible inhibition while preserving the scavenger capacity of plasma BuChE for OPs. By contrast, the non-selective inhibition of AChE and BuChE by pyridostigmine limits the effectiveness of the drug as an antidotal therapy against OP intoxication. We and others have shown that increasing the doses of pyridostigmine beyond a certain level worsens the outcome of animals exposed to lethal doses of OP compounds (Albuquerque et al., Proc. Natl. Acad. Sci. USA 103:13220-13225, 2006). As is discussed below, galantamine also has differential effects inhibiting blood vs. brain acetylcholinesterase.

Galantamine compounds that are useful for treating or preventing organophosphorus (OP) poisoning in a mammal include galantamine, its salts, and biologically active analogs (described in Davis et al., U.S. Pat. No. 6,150,354; and Davis et al., U.S. Pat. No. 6,670,356), naturally-occurring analogs or analogs that have been isolated from natural products (The Alkaloids, R. H. F. Manske editors, Academic Press, N.Y., 15$^{th}$ edition), derivatives (described in Davis et al., U.S. Pat. No. 6,319,919), fragments, variants and chemically-modified forms thereof; hereafter "galantamine." Combinations of any biologically effective form of galantamine can be used in the present invention. Galantamine can be formulated for administration in any manner known in the art as described below, preferably formulated for injection or oral administration. As described below, galantamine can be modified according to known methods in medicinal chemistry to increase its stability, half-life, uptake or efficacy.

The nerve agents soman (3-(fluoro-methyl-phosphoryl) oxy-2,2-dimethyl-butane), sarin (2-(Fluoro-methylphosphoryl)oxypropane), VX (S-2-[diisopropylamino]O— ethyl methylphosphonothioate), tabun (ethyl N,N-dimethylphosphoramidocyanidate) are well known in the art. Less well known are other OP nerve agents referred to as Novichok agents developed by the Soviet Union in the 1980s and 1990s and allegedly the most deadly nerve agents ever made, with some variants supposed to be 5-8× more potent than VX nerve agent. (Vadim J. Birstein, The Perversion Of Knowledge: The True Story of Soviet Science, Westview Press (2004) ISBN 0-813-34280-5; Yevgenia Albats and Catherine A. Fitzpatrick, The State Within a State: The KGB and Its Hold on Russia—Past, Present, and Future, 1994, ISBN 0-374-18104-7 (see pages 325-328)). Novichok agents belong to "third generation chemical weapons" designed as a part of Soviet "Foliant" program. (Chemical Weapons in Russia: History, Ecology, Politics by Lev Fedorov, Moscow, Center of Ecological Policy of Russia, 27 Jul. 1994).

The Novichok agents are organophosphorus compounds with an attached dihaloformaldoxime group, with the general formula shown below, where R=alkyl, alkoxy, alkylamino or fluorine and X=halogen (F, Cl, Br) or pseudohalogen such as C≡N. (Kruglyak Yu et al., Phosphorylated oximes. XII. Reactions of 2-halophospholanes with dichlorofluoronitrosomethane, Zhurnal Obshchei Khimii. 1972; 42(4):811-14; Raevskii O A, et al., Effect of Alkyl Substituents in Phosphorylated Oximes, Zhurnal Obshchei Khimii. 1987; 57(12): 2720-2723; Raevskii O A, et al., Electron-Donor Functions of Ethyl Methylchloroformimino Methylphosphonate, Zhurnal Obshchei Khimii. 1987; 57(9):2073-2078; Makhaeva G F, et al., Comparative studies of O,O-dialkyl-O-chloromethylchloroformimino phosphates: interaction with neuropathy target esterase and acetylcholinesterase, Neurotoxicology, 1998 August-October; 19(4-5):623-8. PMID 9745921; Malygin V V, et al., Quantitative structure-activity relationships predict the delayed neurotoxicity potential of a series of O-alkyl-O-methylchloroformimino phenylphosphonates, Journal of Toxicology and Environmental Health Part A. 2003 Apr. 11; 66(7):611-25, PMID 12746136; and Steven L. Hoenig, Compendium of Chemical Warfare Agents, Springer N.Y., 2007, ISBN 978-O-387-34626-7, incorporated herein by reference).

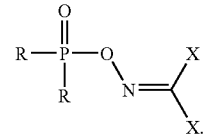

The most potent compounds from this family, Novichok-5 and Novichok-7, are supposedly around 5-8 times more potent than VX; however, the exact structures of these compounds are not publicly available. Some examples of Novichok compounds reported in the literature are shown below.

Binary Novichok compounds were apparently also produced, where two relatively non-toxic compounds would react to form a lethal Novichok agent when mixed, however the details of these are not available.

Galantamine Administration to Treat or Prevent OP Poisoning

Administraation of Galantamine Before OP Exposure

We tested the ability of galantamine to prevent OP poisoning if administered before exposure to highly toxic doses of soman or sarin. We found that galantamine is an effective antidote for treating or preventing OP poisoning when administered up to 5 hours before exposure to highly lethal amounts of $1.5 \times LD_{50}$ to $2.0 \times LD_{50}$ soman or sarin when followed by treatment as soon after exposure with atropine as possible, preferably within 5 minutes. The optimal time for administering galantamine was 30 minutes before exposure to these highly lethal amounts of $1.5 \times LD_{50}$ OP or higher.

As expected, clear signs of cholinergic hyperexcitation, including miosis, increased chewing, hypersalivation, muscle fasciculations, difficulty in breathing, and loss of motor coordination, were evident at 5-15 minutes after the s.c. injection of $1.5 \times LD_{50}$ soman (42 µg/kg of body weight) or sarin (63 µg/kg) in prepubertal male guinea pigs. Although an i.m. injection of atropine (6-16 µg/kg) immediately after the OP challenge attenuated the muscarinic signs, all animals showed tremors and intense convulsions within 15-30 minutes after the challenge. Atropine-treated, OP-challenged guinea pigs were euthanized when they developed life-threatening symptoms. By 24 hours after the exposure to the nerve agents, only 11% of the animals (7 of 65) remained alive.

By contrast, all guinea pigs that received treatment with 5-12 mg/kg galantamine hydrobromide (hereafter referred to as galantamine) 30 minutes before s.c. injection of $1.5 \times LD_{50}$ soman or sarin, followed by post-OP exposure treatment with 10 mg/kg atropine survived at 24 hours. The $ED_{50}$ values of galantamine for survival at 24 hours for animals exposed to $1.5 \times LD_{50}$ soman or sarin were $1.82 \pm 0.37$ or $2.2 \pm 0.50$ mg/kg, respectively (FIG. 1A and FIG. 1B).

The optimal dosage of galantamine changed as the OP levels increased. For example, in animals post-treated with 10 mg/kg atropine, the $ED_{50}$ for galantamine to prevent the lethality of $2.0$ $LD_{50}$ soman was $5.1 \pm 0.66$ mg/kg (mean±SEM; n=8-10 animals per group), with 100% 24-h survival being achieved with a minimum of 8 mg/kg (FIG. 1A). Effective doses of galantamine were well tolerated. Only animals that received 16-20 mg/kg galantamine showed mild adverse symptoms which lasted 10-15 minutes and included increased chewing, hypersalivation, fasciculations, and tremors.

Muscarinic blockade by atropine administered shortly after OP exposure contributed to the antidotal effectiveness of galantamine therapy for lethal doses of exposure to highly lethal amounts of sarin or soman of about $1.5 \times LD_{50}$ or more. Animals that were pretreated before exposure to $1.5 \times LD_{50}$ soman or sarin with 5 or 8 mg/kg galantamine followed after exposure by approximately 5.5 mg/kg atropine had a 50% reduction of lethality. In the first 24 hours, less than 2% of the guinea pigs that were treated exclusively with this dose of atropine survived an exposure to $1.5 \times LD_{50}$ OP. The surviving animals showed 5-10% weight loss within the first 24 hour after exposure to the OP and did not recover their weight. The other 98% of the OP-challenged guinea pigs had life-threatening symptoms within 5-30 minutes after the OP challenge and were euthanized as per the IACUC-approved protocol for animal care and handling. An unexpected synergistic interaction occurred between galantamine and atropine in an amount of 6 mg/kg or higher. We found that increasing the dose of galantamine from 5 to 8 mg/kg decreased the dose of atropine needed to protect the animals from the toxicity of $1.5 \times LD_{50}$ soman (FIG. 1C). Doses of galantamine and atropine required to treat OP intoxication may be optimized by using response-surface methods (Carter, W. H., Jones, D. E. & Carchman, R. A. (1985) *Fundam. Appl. Toxicol.* 5, S232-S241), incorporated herein by reference. In most of our experiments we administered 10 mg atropine, however we have successfully used 12 mg in guinea pigs. It is emphasized that these amounts may vary in humans. When actual human data is obtained, the amounts of both galantamine and atropine may need to be adjusted.

Figure 2A:
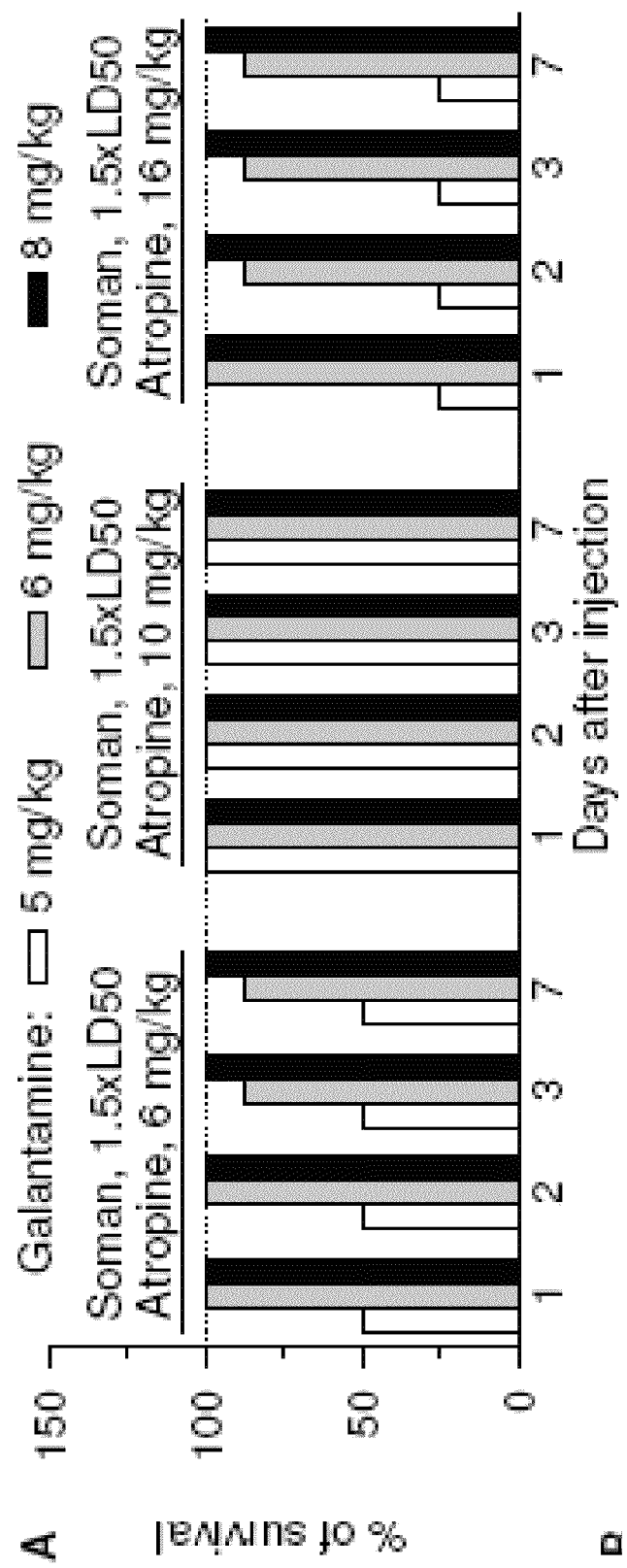
FIG. 2 Long-term effectiveness and acute toxicity of different antidotal therapies against OP poisoning. (A) Seven-day survival of guinea pigs treated with galantamine at 30 minutes before and atropine at 1 minute after their challenge with $1.5 \times LD_{50}$ soman. Each group had 8-12 animals. (B) Seven-day follow-up of the weight of animals subjected to different treatments. Weights are expressed as percent of the weights measured 1 hour before a treatment. Control groups consist of animals that received a single i.m. injection of atropine, galantamine, huperzine, or saline. The soman/atropine groups consist of animals treated with galantamine or huperzine at 30 minutes before and atropine at 1 minute after soman (n=5-8 animals per treatment). (C) Graphs of the average total distance traveled and stereotypy of guinea pigs in an open-field arena at the indicated times after they received an i.m. injection of saline, galantamine, or huperzine (n=6 animals per treatment). In B and C, results are presented as the mean plus or minus SEM. Asterisks indicate that results from huperzine- and saline-treated animals are significantly different at P is less than or equal to 0.05 (ANOVA followed by Dunnett's post hoc test).

All animals survived the first 24 hours after the $1.5 \times L_{D50}$ soman challenge when they were pretreated with 6 mg/kg galantamine 30 minutes before exposure and post-treated with 6 mg/kg atropine 1 minute after exposure; however, only 80% of them remained alive after the 3rd day post-OP exposure (FIG. 2A). Quite unexpectedly we discovered that survival remained at 100% in animals pretreated with 5-8 mg/kg galantamine and post-treated with a slightly higher dose of atropine, i.e. 10 mg/kg, for the entire one week post-exposure observation period. Increasing the dose of atropine to 16 mg/kg reduced the acute and long-term efficacy of doses of galantamine 8 mg/kg (FIG. 2A). Thus, 10 mg/kg atropine ensured the highest long-term effectiveness of galantamine against the toxicity of $1.5 \times LD_{50}$ soman in combination with galantamine. Atropine is available from Sigma Chemical Co. (St. Louis, Mo.), and other suppliers in a form suitable for human use.

We further studied the weight gain pattern in animals treated with galantamine (5-8 mg/kg i.m.) administered 30 minutes before exposure to $1.5 \times LD_{50}$ soman or sarin s.c. followed by atropine 10 mg/kg administered i.m. 1 minute after the nerve agent. The rate of weight gain of these animals over an 8-day post-exposure period was similar to that observed in controls treated with galantamine alone for all doses. This is an indication that pre-exposure treatment with galantamine followed by post-exposure administration of atropine was highly effective in preventing OP poisoning and maintaining normal physiology even after exposure to highly lethal levels of the nerve agent.

The acute toxicity of another OP compound, paraoxon—the active metabolite of the pesticide parathion—was also effectively counteracted by pre-treatment with galantamine and post-OP exposure administration of atropine. All guinea pigs treated with atropine alone (10 mg/kg, i.m.) immediately after their exposure to 1.8 mg/kg paraoxon developed life-threatening symptoms and were euthanized. By contrast, all atropine-treated animals survived with no signs of toxicity when they received galantamine (8 mg/kg, i.m.) 30 minutes before their exposure to 2 mg/kg paraoxon (FIG. 1D). Further, galantamine-atropine-treated animals that survived the challenge with 3 mg/kg paraoxon (FIG. 1D) displayed only brief, mild signs of intoxication that included increased chewing and slight tremors.

In another experiment we found that only a fraction (about 30-60%) of animals pretreated with pyridostigmine (26-65 µg/kg) and post-treated with 10 mg/kg atropine survived the challenge with $1.5 \times LD_{50}$ soman (FIG. 1E). The effectiveness of this therapy increased as the dose of pyridostigmine was raised to 52 µg/kg (FIG. 1E). However, increasing the dose of pyridostigmine to 65 µg/kg decreased the effectiveness of the treatment, most likely because the potential benefit of increasing the protection of AChE from the actions of OPs is counteracted and eventually outweighed by the simultaneous pyridostigmine-induced inhibition of BuChE, an enzyme that serves as an endogenous scavenger of OPs (Doctor, B. P., et al. (1991) Neurosci. Biobehav. Rev. 15, 123-128).

The safety of the antidotal therapy using pre-treatment with galantamine and post-treatment with atropine was also greater than that of a combination of huperzine and atropine. Approximately 80% of the animals challenged s.c. with $1.5 \times LD_{50}$ soman survived if they were pretreated with 100-200 µg/kg huperzine and post-treated with 10 mg/kg atropine; the minimum dose of huperzine needed to provide 100% survival of soman-challenged, atropine-treated guinea pigs was 300 µg/kg (FIG. 1E). However, at doses $\geq 300$ µg/kg, huperzine triggered transient, albeit incapacitating side effects that included profuse secretions, muscle fasciculations, abnormal gait, tremors, and respiratory distress. The stereotypic behavior of animals treated with huperzine was quantitatively analyzed in an open-field arena, as described in Albuquerque et al. (Proc. Natl. Acad. Sci. 103: 13220-13225, 2006), which reference is incorporated in its entirety as if fully set forth herein.

Figure 3:
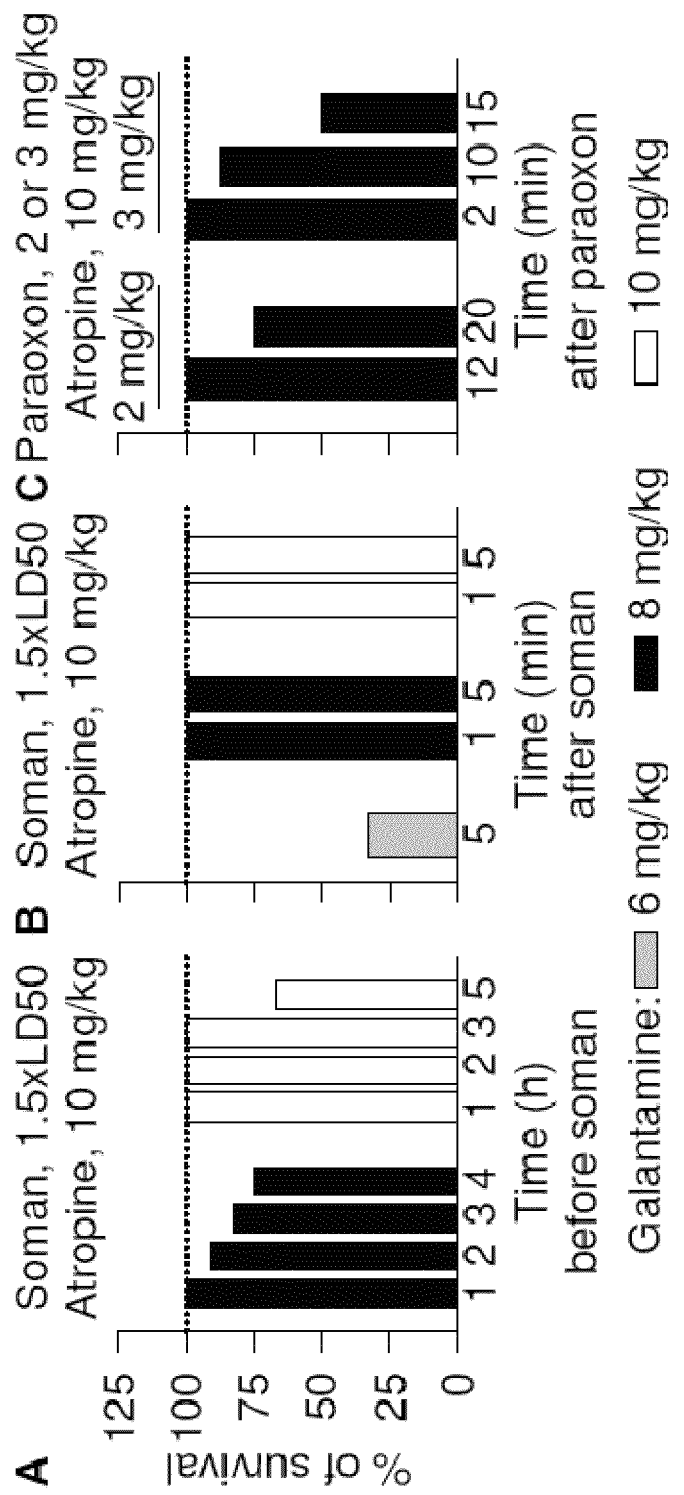
FIG. 3 Efficacy of galantamine as pre- or post-treatment for OP poisoning is dose- and time-dependent. (A) Twenty-four-hour survival of animals that received a single i.m. injection of 8 or 10 mg/kg galantamine at 1, 2, 3, 4, or 5 hours before the s.c. injection of $1.5 \times LD_{50}$ soman that was followed 1 minute later by an i.m. injection of 10 mg/kg atropine. (B and C) Twenty-four-hour survival of animals that received a single i.m. injection of specific doses of galantamine at different times after their challenge with $1.5 \times LD_{50}$ soman or 2-3 mg/kg paraoxon, respectively. Each group had 8-10 animals.

An effective antidotal therapy should afford long-lasting protection for first responders who will attend to a population acutely exposed to toxic levels of OPs. Thus, experiments were designed to determine how long before an exposure to OPs an acute pre-OP exposure treatment with galantamine would remain effective with 10 mg/kg atropine administration post-OP exposure. All guinea pigs that received 8 mg/kg galantamine up to 1 hour before $1.5 \times LD_{50}$ soman followed with atropine 1 minute after exposure survived with no signs of toxicity (FIG. 3A). As the interval between the injections of galantamine and soman increased beyond 1 h, the survival decreased (FIG. 3A Black bars). Increasing the dose of galantamine to 10 mg/kg prolonged the time within which the antidotal therapy remained effective (FIG. 3A) so that there was 100% survival if galantamine was administered up to 3 hours before exposure to soman; by 5 hours survival dropped to about 65%. (FIG. 3A). Nonetheless, if a crisis prevents administration of galantamine until 5 hours after exposure, 65% survival is better than no treatment at all.

Based on these observations, certain embodiments of the invention are directed to methods for treating or preventing OP poisoning caused by exposure to highly lethal amounts of $1.5 \times LD_{50}$ or more of an OP nerve agent by administering galantamine, preferably in an amount from about 6-10 mg up to about 5 hours before exposure, preferably within 1 hour of exposure, followed by a muscarinic receptor antagonist, such as atropine, in an amount of about 1 to about 12 mg as soon after exposure as possible, preferably within 5 minutes. Because nerve agents reduce acetylcholinesterase activity so drastically, the amount of galantamine should be an amount that effectively competes with the nerve agent for binding to acetylcholinesterase but avoids the risk of depressing acetylcholinesterase to lethal levels. This amount is typically an amount up to about 10 mg, preferably 6-10 mg. As the experiments described below will show, galantamine maintained the long term survival of OP-challenged animals with no significant adverse effects including brain damage. Data from treating humans with the therapies of the present invention may involve adjustments in the dosage of galantamine and atropine.

Where the OP is a pesticide (instead of nerve agent) and the dose of exposure is highly lethal (about $1.5 \times LD_{50}$ or higher), slightly higher doses of galantamine of about 6 to up to about 12 mg can be administered without the risk of depressing acetylcholinesterase to a lethal level, followed by atropine treatment. We will show below that if exposure is to about $1 \times LD_{50}$ or less, then no muscarinic receptor antagonist is needed.

OP pesticides include those listed below, all of which come within the scope of the present invention: Acephate, Azamethiphos, Azinphos ethyl, Azinphos methyl, Bromophos, Bromophos ethyl, Cadusofos, Carbophenylhion, Chlormephos, Chlorphoxim, Chlorpyrifos, Chlorpyrifos-methyl, Chlorthiophos, Chlorvinohos, Coumaphos, Crotoxyphos, Crufomate, Cyanofenphos, Cyanophos, Demephron —O and —S, Demeton —O and —S, Demeton-S-methyl, Demeton-S-methylsulphon, Dialifos, Diazinon, Dichlofenthion, Dichlorvos, Dicrotophos, Dimefox, Dimethoate, Dioxabenzophos, Dioxathion, Disulfoton, Ditalmifos, Edifenphos, EPBP, EPN, ESP, Ethion, Ethopropos, Etrimfos, Famphur, Fenamiphos, Fenchlorphos, Fenitrothion, Fensulfothion, Fenthion, Fonofos, Formothion, Fosmethilan, Heptenophos, Isazofos, Isofenphos, Isothioate, Isoxathion, Jodfenphos, Leptophos, Malathion, Menazon, Mephosfolan, Methacrifos, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phospholan, Phoxim, Pirimiphos-ethyl, Pirimiphos-methyl, Profenofos, Propaphos, Propetamphos, Prothiofos, Prothoate, Pyraclofos, Pyridaphenthion, Quinlphos, Schradan, Sulfotep, Sulprofos, Temephos, TEPP, Terbufos, Tetrachlorvinphos, Thiometon, Thionazin, Triazophos, Trichlorfon, and Vamidothion.

OPs can persist in the blood stream for days after exposure. Therefore, after exposure to highly lethal amounts of either nerve agents or pesticides (more than about $1.5 \times LD_{50}$), a preferred embodiment includes continuing galantamine therapy for up to a month or even longer after exposure to prevent nerve damage and diseases such as IMS. In a preferred embodiment additional doses of galantamine are administered up to three times per day. In one embodiment, the additional doses of galantamine are in an amount of from about 3 to about 8 mg, preferably 3-6 mg, for up to a month after exposure to the highly lethal doses of OP. In a preferred embodiment the amount of galantamine is reduced on about day 4 post-exposure to about 3 to about 4 mg up to three times per day for long-term administration.

In some cases, prevention or treatment of the muscarinic syndrome component of OP poisoning with highly lethal amounts of OP may require more than one administration of the muscarinic receptor antagonist, preferably atropine. Therefore, in certain embodiments additional doses of the muscarinic receptor antagonist are administered as frequently as needed for as long as any symptoms appear. In a preferred embodiment, additional doses of the muscarinic receptor antagonist are administered about every 3 to 5 minutes after the first post-exposure administration for as long as any symptoms of muscarinic syndrome appear. In some embodiments, these subsequent administrations of atropine are in a lower amount of from about 1 to about 2 mg.

In the situation where a soldier or civilian may be exposed to a terrorist attack of highly lethal doses of OP (about 1.5× $LD_{50}$ or more) at any time, it is recommended that the he or she be on a regimen of galantamine, in a prophylactic amount of from about 6 mg to about 10 mg, preferably by oral administration, up to three times per day while at risk of such an attack. Because galantamine has no adverse effects at this dose, it can be chronically administered to minimize the damage of exposure to lethal doses of OP.

In a preferred embodiment, galantamine is a pharmaceutically acceptable salt including the hydrobromide salts, hydrochloride salts, methylsulfate salts and methiodide salts. Galantamine and atropine can be administered by any route, including intramuscular injection, subcutaneous injection, intranasal or oral administration. Atropine is administered at therapeutic doses, preferably in the range of about 1 to about 12 mg. (Human & Experimental Toxicology, Vol. 20, No. 1, 15-18 (2001), incorporated herein by reference). The preferred route for administration in a crisis situation, war or terrorist attack, is i.m. injection. Intravenous injection of atropine is potentially dangerous and therefore has to be done by a professional. In a preferred embodiment, galantamine and atropine are administered at the same time, preferably in a single pharmaceutical formulation. Another embodiment of the invention is directed to a pharmaceutical formulation that includes both galantamine, preferably from about 6 to about 10 mg galantamine and a muscarinic receptor antagonist, preferably atropine from about 1 to about 12 mg.

Atropine, a muscarinic receptor antagonist that reduces the activity of the muscarinic acetylcholine receptor, is the most commonly used antimuscarinic agent. Atropine is preferable to some other muscarinic receptor antagonists because it has the fewest CNS effects. Other agents that have properties similar to atropine at muscarinic receptors can also be used in conjunction with galantamine in the present invention. Some muscarinic receptor antagonists such as scopolamine can have CNS incapacitating effects and therefore must be used with caution. Other muscarinic receptor antagonists that have been reported as useful in treating or preventing OP poisoning include telenzepine, AF-DX116 [11-(2-[(diethylamino)methyl]-1-piperidinyl acetyl)-5,11-dihydro-6H-pyrido 92.b-b) (1,4)-benzodiazepin-6-one], and biperiden (0.1-10 microM) (Harrison P K, et al., J Pharmacol Exp Ther. 2004 August; 310(2):678-86. Epub 2004 Mar. 18), incorporated herein by reference. These agents can also be used in certain embodiments of the present invention. Oxime compounds can also be used with galantamine as post-exposure therapy. Oximes can reactivate acetylcholinesterate by attaching to the phosphorus atom and forming an oxime-phosphonate which then splits away from the acetylcholinesterase molecule. The most effective oxime nerve-agent antidotes are pralidoxime (also known as 2-PAM), obidoxime, methoxime, HI-6, Hlo-7, and TMB-4. (Eyer P, Toxicol Rev. 2003; 22(3):165-90, incorporated herein by reference).

Long term nerve damage from IMS can appear several weeks after OP exposure, particularly to lethal amounts of OPs. Therefore certain embodiments are directed to treating or preventing IMS in a subject at risk of developing it or having the disease, by administering a therapeutically effective amount of galantamine, preferably in an amount of from about 3 to 10 mg up to three times per day for up to a month after exposure to the OP or even longer, whether the OP is a nerve agent or pesticide. As long as symptoms appear, the amount of galantamine is preferably from 3 to 10 mg per dose. However, if there are no symptoms, in a preferred embodiment, galantamine is administered at a maintenance dose for example of about 3-6 mg up to three times per day for long term therapy up to a month or more after the exposure.

Galantamine Maintains Long-Term Survival of OP-Challenged, Atropine-Treated Guinea Pigs and Has No Significant Effect on Gross Behavior of the Animals: Comparison with Huperzine.

Figure 2B:
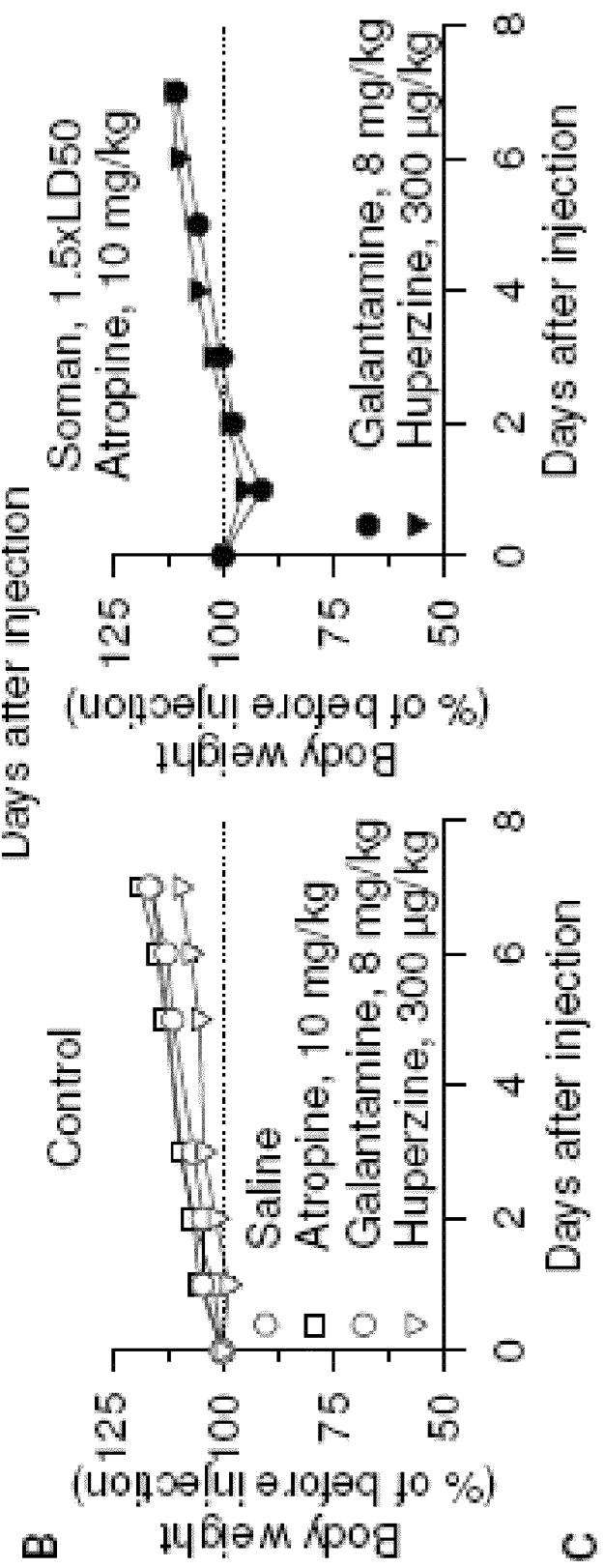

Within 1 week after a single i.m. injection of saline, galantamine (8 mg/kg) without atropine, or atropine (10 mg/kg) without galantamine, guinea pigs gained weight at similar rates, i.e., 2.51±0.11% per day, 2.30±0.05% per day, and 2.37±0.03% per day (FIG. 2B). In contrast, guinea pigs that received a single i.m. injection of huperzine (300 µg/kg) gained weight at a rate of 1.72±0.17% per day (FIG. 2B), which is significantly slower than that measured for saline-injected animals (p<0.01 compared with saline-injected animals according to ANOVA followed by Dunnett's post hoc test).

Animals treated with 8 mg/kg galantamine 30 minutes before exposure to 1.5×$LD_{50}$ soman and post-treated with 10 mg/kg atropine lost, on average, 10% of their body weight at 24 hours after the OP exposure (FIG. 2B), but their rate of weight gain during the remaining recovery period (2.72±0.26% per day; mean±SEM; n=5 animals) was not significantly different from that of saline-treated animals that were not challenged with soman. Galantamine treatment 30 minutes before exposure followed after exposure with atropine, was equally effective in maintaining the rates of weight gain of guinea pigs challenged with 1.5×$LD_{50}$ sarin or 3 mg/kg paraoxon (data not shown) at 2.53±0.20% per day or 2.66±0.21% per day (mean±SEM; n=3-5 animals per group), respectively. The acute toxicity of huperzine was not reflected in the rates of weight gain of animals that survived the OP challenge (FIG. 2B). Although mortality was high with huperzine, those animals that survived gained weight at a rate similar to the galantamine-treated animals.

Figure 2C:
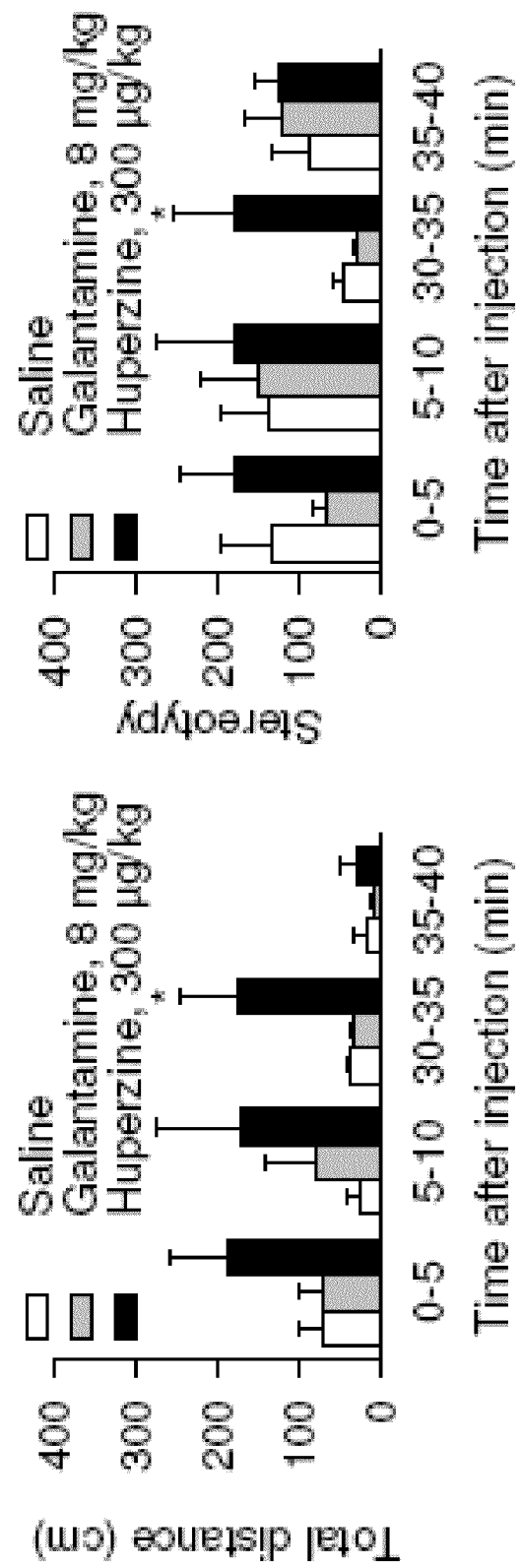

In an attempt to quantify potential untoward behavioral effects of the doses of galantamine and huperzine needed to prevent acute OP poisoning, the overall ambulatory activity of guinea pigs was examined in an open-field arena. Previous studies reported that other centrally acting acetylcholinesterase inhibitors, including physostigmine, decrease locomotor activity and stereotypic behavior of rodents in the open field (Silvestre, J. S., et al. (1999) Pharmacol. Biochem. Behav. 64, 1-5). Further, inhibition of the NMDA type of glutamate receptors, a mechanism that appears to contribute to the effectiveness of huperzine in preventing OP toxicity (Gordon, R. K., et al. (2001) J. Appl. Toxicol. 21, S47-S51), is known to increase stereotypy in rodents (Koek, W., et al. (1988) J. Pharmacol. Exp. Ther. 245, 969-974). Each guinea pig, immediately after receiving an i.m. injection of saline, galantamine (8 mg/kg), or huperzine (300 µg/kg), was placed in an open-field arena equipped with infrared sensors. At the dose tested, galantamine had no significant adverse effect on the overall locomotor activity of guinea pigs (FIG. 2C). However, huperzine adversely increased the locomotor activity of the animals in a way that became significant at 30 minutes after the treatment at which time a distinct pattern of locomotor stereotypy, including repetitive routes of locomotion in the open-field arena, was also significantly higher in huperzine-treated than in saline-treated animals (FIG. 2C).

Efficacy of Galantamine Administered After Exposure to Highly Lethal Amounts of OP (About 1.5×$LD_{50}$ OP or Higher)

Considering the difficulty of predicting when a person will be exposed to toxic levels of OPs under battlefield conditions, in the case of a terrorist attack or during handling of pesticides, experiments were also designed to determine whether post-OP exposure treatment with galantamine and atropine could effectively counteract the acute toxicity of OPs. We found that all animals treated with 8 or 10 mg/kg galantamine up to 5 minutes after challenge with $1.5 \times LD_{50}$ soman and with 10 mg/kg atropine 1 minute after exposure survived (FIG. 3B) with no signs of intoxication. The rate of weight gain and gross behavior of these animals were indistinguishable from those of saline-treated animals that were not exposed to soman. Guinea pigs that received 10 mg/kg atropine and 8 mg/kg galantamine at 1 and 5 min, respectively, after $1.5 \times LD_{50}$ soman or sarin did not show any peripheral and central hypercholinergic signs of OP intoxication, such as hypersecretion, muscle contraction, respiratory difficulties, convulsion, or behavioral abnormalities. Further, during the observation period of up to 1-2 weeks, they showed no signs of ill health. By contrast, all guinea pigs that were post-treated with atropine alone presented severe signs of intoxication within 10-20 minutes. Only 11% of these guinea pigs survived for 24 hours after the nerve agent exposure.

Post-treatment with galantamine/atropine also prevented the acute toxicity of supralethal doses of paraoxon (FIG. 3C). Twenty-four-hour survival of animals that received a single i.m. injection of various amounts of galantamine at different times after their challenge with 2 mg/kg paraoxon, show that 8 mg galantamine given 12 minutes after exposure and 10 mg atropine given at 1 minute after the OP was 100% effective. When galantamine was given 20 minutes after the exposure to 2 mg/kg paraoxon, 75% of the animals survived. The therapeutic window of time within which post treatment with 8 mg galantamine followed by 10 mg atropine remained effective in sustaining 100% survival of the animals decreased as the dose of paraoxon increased (FIG. 3C). For 3 mg paraoxon, 8 mg galantamine was 100% effective at 2 minutes, but 90% at 10 minutes and 50% at 15 minutes.

Based on these observations, certain other embodiments of the invention are directed to methods for treating or preventing OP poisoning caused by exposure to $1.5 \times LD_{50}$ or higher doses of an OP nerve agent by administering galantamine in an amount from about 6-10 mg up to 30 minutes after exposure (preferably within 15 minutes of exposure, more preferably within 5 minutes), followed by a muscarinic receptor antagonist like atropine in an amount of about 1 to about 12 mg as soon after exposure as possible, preferably within 5 minutes. Again, because nerve agents reduce acetylcholinesterase activity so drastically, the amount of galantamine should be high enough to effectively compete with the nerve agent for binding to acetylcholinesterase without depressing acetylcholinesterase to lethal levels. This amount can vary according to the amount and type of OP exposure, but in a preferred embodiment up to about 10 mg galantamine is administered after exposure to highly toxic levels of nerve agents, preferably 6-10 mg. The window of opportunity for administering galantamine after exposure is different for different OPs, therefore if the exposure is to an unknown nerve agent or combination of nerve agents, for example in a war or other terrorist situation, administration should be as soon after exposure as possible.

As before, where the OP is an pesticide and the dose of exposure is to about $1.5 \times LD_{50}$ or higher, slightly higher doses of galantamine of 6 to up to 12 mg can be administered up to 30 minutes after exposure without the risk of depressing acetylcholinesterase to a lethal level, followed by atropine treatment. The amount may vary once actual human data is obtained.

As before, after exposure to highly lethal amounts of either nerve agents or pesticides (more than about $1.5 \times L_{D50}$), a preferred embodiment includes continuing galantamine therapy for up to a month or even longer after exposure to prevent nerve damage and diseases such as IMS. In a preferred embodiment additional doses of galantamine are administered up to three times per day, for example in an amount of 3 to about 6 mg, for up to a month after exposure to the highly lethal doses of OP. In a preferred embodiment the amount of galantamine is reduced on about day 4 post-exposure to about 3 to about 4 mg up to three times per day for long-term administration. In some cases, prevention or treatment of the muscarinic syndrome component of OP poisoning with highly lethal amounts of OP may require more than one administration of the muscarinic receptor antagonist. Therefore, in certain embodiments additional doses of the muscarinic receptor antagonist, preferably atropine, are administered as frequently as needed for as long as any symptoms appear. In a preferred embodiment, additional doses of atropine are administered about every 3 to 5 minutes after the first post-exposure atropine administration for as long as any symptoms of muscarinic syndrome appear. In some embodiments, these subsequent additional administrations of atropine are in a lower amount of from about 1 to about 2 mg.

The pharmacokinetic studies presented below show that after an i.m. injection of 8 mg/kg galantamine, plasma and brain levels of the drug peaked between 5 and 30 minutes. Thus we estimate based on galantamine's molecular weight of 287.4, that the minimal plasma concentration of galantamine needed to prevent OP toxicity and lethality is about 2.8 µM. Doses of galantamine recommended for treatment of patients with Alzheimer's disease are between 8 and 24 mg/day (Corey-Bloom supra), and peak plasma concentrations of 0.2-3 µM have been detected in healthy human subjects treated orally or s.c. with a single dose of 10 mg of galantamine (Bickel supra; and Mihailova, D, (1989) *Pharmacology* 39, 50-58). Therefore, in certain embodiments, the therapeutically effective amount of galantamine needed to treat or prevent OP poisoning before or after exposure to any dose of OP is an amount that achieves a plasma galantamine level of about 2 to about 3 µM. This amount will vary depending on the OP agent and the time of galantamine administration.

There is no opportunity to conduct experiments with OPs on humans, however, experience gained in the field from treating subjects exposed to highly toxic levels of nerve agents or pesticides may result in changes to the preferred amounts of galantamine and atropine.

Figure 4A:
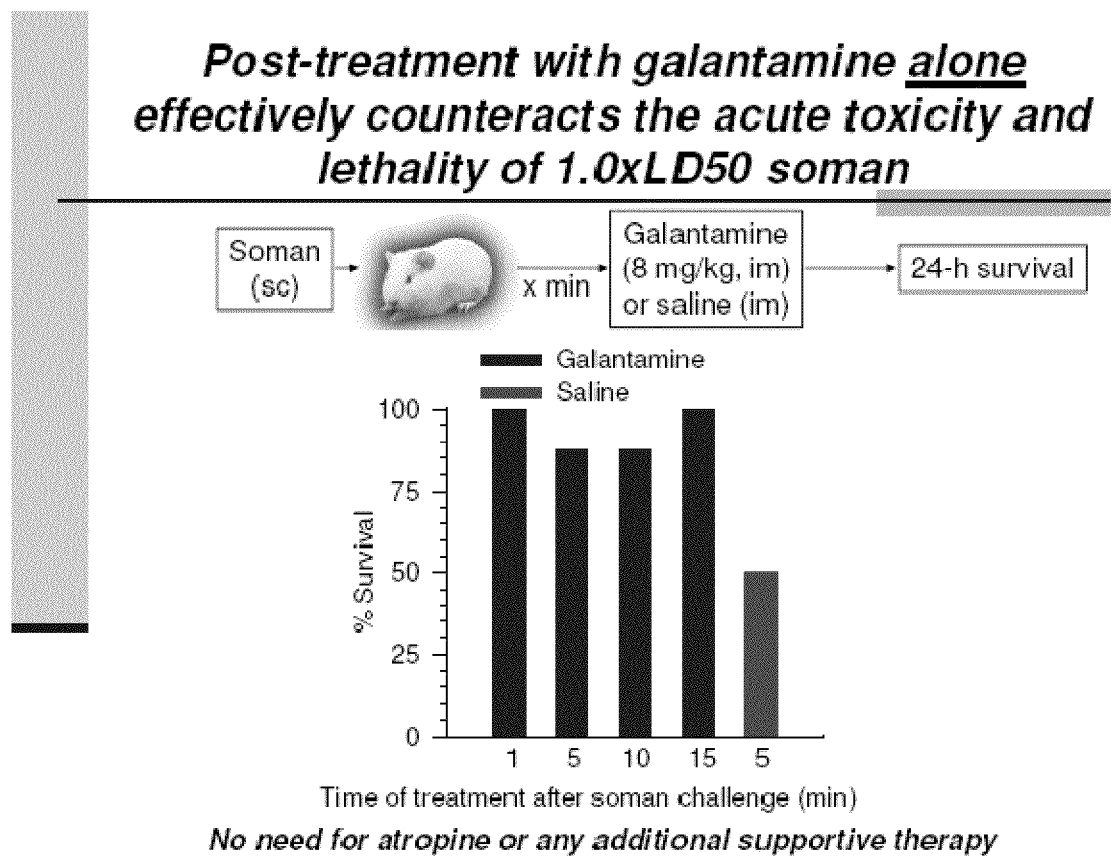
FIG. 4 Treatment with galantamine after exposure to 1.0 $LD_{50}$ (FIG. 4A) or after exposure to 0.5 $LD_{50}$ (FIG. 4B) is effective by itself, without atropine, in treating or preventing organophosphorus poisoning.

Galantamine Alone is Effective When Administered After Exposure to OP Doses of About $1.5 \times LD_{50}$ or Lower In this series of experiments we tested the efficacy of galantamine administered after exposure to lethal doses of soman as high as $1 \times LD_{50}$, and to sublethal doses of about $0.6 \times LD_{50}$. Our results showed that 50% of the animals treated with saline alone were dead by 24 hours after exposure to $1 \times LD_{50}$. By contrast, treatment with 8 mg/kg i.m. galantamine alone following $1 \times LD_{50}$ soman exposure, effectively counteracted the acute toxicity and lethality of the poison if administered within 15 minutes (85-100% survival at 24 hours). FIG. 4A. The soman ($1 \times LD_{50}$)—challenged animals that were post-treated with galantamine (8 mg/kg, im) survived with no sign of intoxication. These animals were followed up to 14 days, during which time the observation period, they gained weight at the same rate as saline-injected guinea pigs.

Figure 4B:
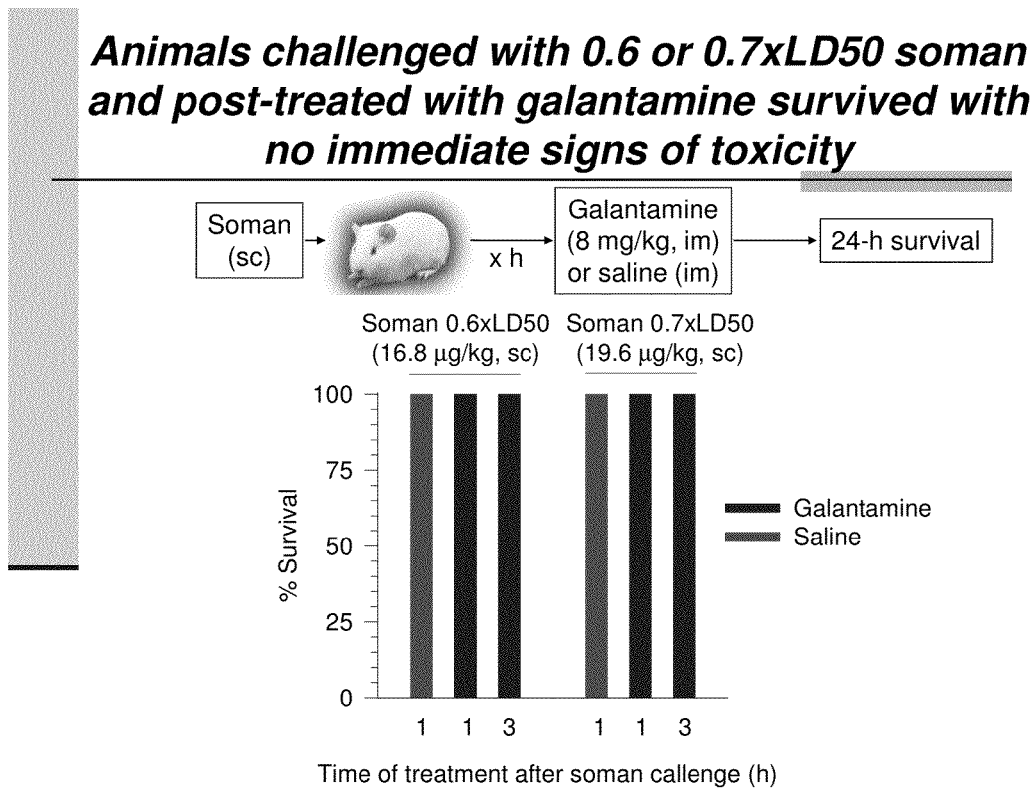

Galantamine administered in an amount of 8 mg/kg i.m. within 1-3 hours after exposure to a lower dose of 0.6 $LD_{50}$ (16.8 µg/kg, s.c.) or 0.7 $LD_{50}$ (10.6 µg/kg, s.c.) resulted in 100% survival at 24 hours with no immediate signs of toxicity. The ability of galantamine alone to counteract low dose OP exposure up to 3 hours after exposure is relevant for therapies to treat or prevent low dose OP poisoning, for example by chronic exposure to pesticides, or victims on the fringe of a nerve agent attack, i.e. not at the epicenter of the attack. FIG. 4B. Each of the test groups consisted of 10 animals that were continuously observed for 14 days after the OP exposure. The galantamine-treated, soman-exposed animals showed no signs of toxicity and gained weight at the same rate as saline-injected guinea pigs.

Thus, certain embodiments are directed to methods for treating or preventing OP poisoning caused by exposure to amounts of OP of about $1.0 \times LD_{50}$ or less, by administering galantamine alone in an amount of about 6 to about 10 mg whether the OP is either a nerve agent or a pesticide. If the exposure is to a dose of about $1 \times LD_{50}$, then administration is preferred within the first 15 minutes after exposure, preferably as soon after exposure as possible. If exposure is to a sublethal dose of OP either nerve agent or pesticide, then the therapeutic window is larger and galantamine can be administered within 3 hours after exposure. As described above, a preferred embodiment includes administering additional doses of galantamine after exposure to a lethal dose of OP. Even if the dose is sublethal, a preferred embodiment includes additional doses of galantamine after the first post-exposure administration. In a preferred embodiment, additional doses of galantamine given after exposure to sublethal amounts of OPs are amounts of about 3-6 mg, preferably 3-4 mg, up to three times per day for up to three days. Longer treatment is typically not needed for exposure to sublethal doses of OP, but can be optionally added. Galantamine can be administered up to a day before exposure to sublethal doses of OP to prevent OP poisoning.

Another embodiment is directed to a method for treating or preventing organophosphorus poisoning in a human subject such as an agricultural worker or worker in a factory who works with or is exposed to sublethal doses of OP pesticides (less than about $0.8 \times LD_{50}$) on a recurring basis. In this embodiment galantamine or a salt thereof, or a biologically active analog, derivative, fragment or variant thereof is given up to three times per day in an amount of from about 3 to about 6 mg, preferably 3-4 mg for the duration of the risk. In a preferred embodiment galantamine is continued after the risk period ends for up to a week, preferably about 3 days after any risk of exposure has passed. If exposure is to a very low does of an OP, particularly a pesticide, it is possible that doses of galantamine as high as about 24 mg/administration could be therapeutically effective.

Figure 5:
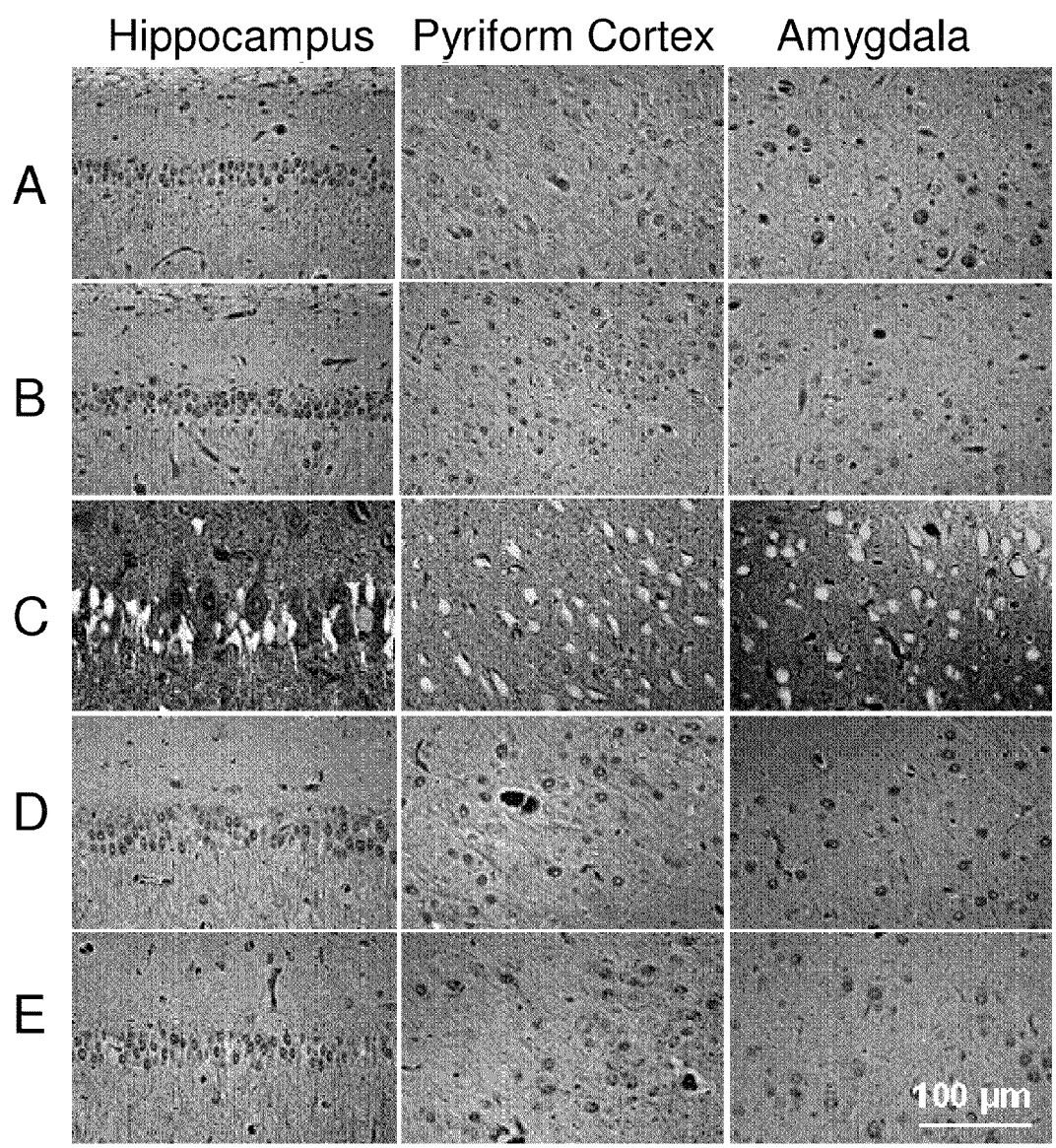
FIG. 5 Soman-induced neurodegeneration is not present in the hippocampus, pyriform cortex, and amygdala of guinea pigs pre- or post treated with galantamine. (A and B) Representative photomicrographs of the hippocampal CA1 field, the pyriform cortex, and the amygdala of guinea pigs that were euthanized 24 hours after an i.m. injection of saline (A) or 8 mg/kg galantamine (B). No FJ-B-positive neurons were seen in the brains of these animals. (C) Large numbers of FJ-B-positive neurons were seen in all three index areas of the brain of a guinea pig that survived for 24 hours after the challenge with 1.5×LD50 soman. (D and E) FJ-B-positive neurons were rarely seen in brain sections of animals that received galantamine (8 mg/kg, i.m.) at 30 minutes before (D) or 5 minutes after (E) soman. In C-E, all animals received atropine (10 mg/kg, i.m.) at 1 minute after the OP, and they were euthanized at 24 hours after the OP challenge. Photomicrographs are representative of results obtained from each group, which had five animals.
Figure 10:
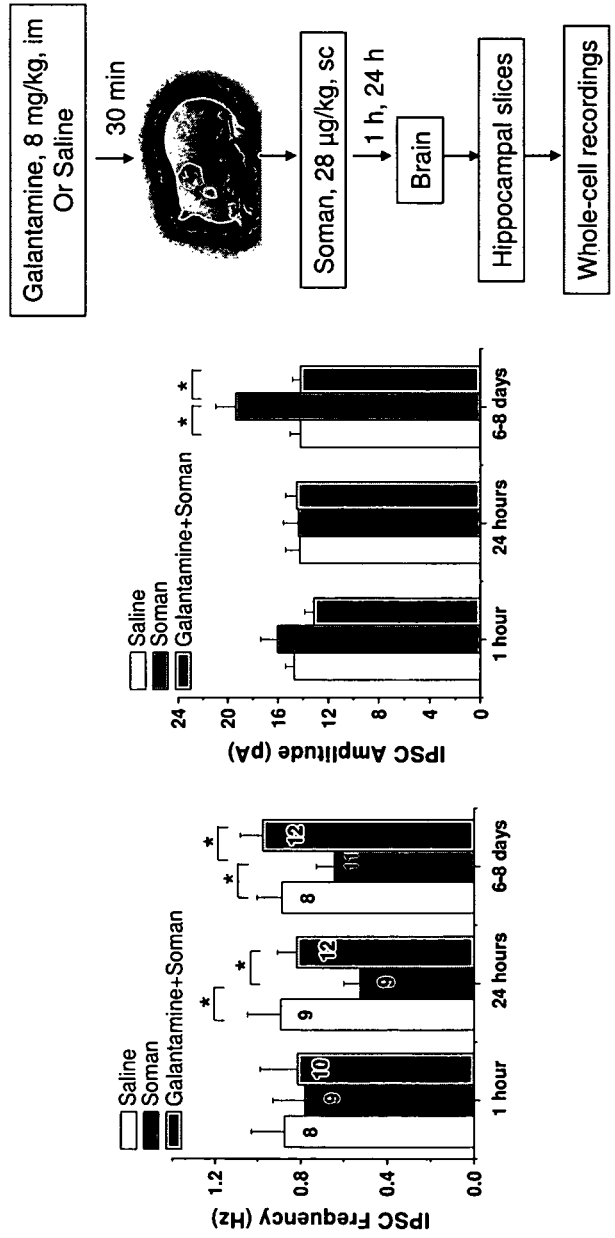
FIG. 10 Soman-induced inhibition of GABAergic transmission is not observed in the hippocampus of galantamine-treated guinea pigs.

No Signs of Neurotoxicity in the Brains of Atropine-Treated Guinea Pigs that Received Galantamine Before or after Soman Challenge Neurodegeneration in three areas of the brain, the pyriform cortex, the amygdala, and the hippocampus, is characteristic of OP intoxication. There were no signs of brain damage at 24 hours after an i.m. injection of saline (FIG. 5A), 8 mg/kg galantamine (FIG. 5B), or 10 mg/kg atropine (data not shown). Galantamine is a critical component of the antidotal therapy regimen because atropine alone was unable to prevent the well described neuronal death triggered by $1.5 \times LD_{50}$ soman (FIG. 5C). Large numbers of shrunken neurons (labeled with Fluoro-Jade B (FJ-B), an anionic fluorescein derivative that binds with high affinity to degenerating cells), were consistently seen in the hippocampus, amygdala, and pyriform cortex of guinea pigs treated with 10 mg/kg atropine 1 minute after OP (no galantamine) that survived for 24 hours after a challenge with $1.5 \times LD_{50}$ soman (FIG. 5C). In contrast, staining with FJ-B was rarely seen in brain sections of soman-challenged animals treated with 8 mg/kg galantamine 30 minutes before or 5 minutes after the OP followed by atropine treatment (FIGS. 5 D and E). Further, the edema observed in the hippocampus and the marked parenchymal spongy state of the amygdala and pyriform cortex of soman-exposed, atropine-treated animals were absent in animals that received galantamine 30 minutes before or 5 minutes after the nerve agent (FIG. 5 C-E). See also FIG. 10 which shows that soman-induced inhibition of GABAergic transmission is not observed in the hippocampus of galantamine-treated guinea pigs.

Figure 6:
FIG. 6 Acute exposure to $1.25 \times LD_{50}$ soman induces brain atrophy.

Using Magnetic Resonance Imaging (MRI), we measured an increase of about 10-14% in ventricular CSF seven days after exposure of guinea pigs to $1.25 \times LD_{50}$ soman (35 µg/kg, s.c.) (FIG. 6). In addition, T2-weighted images of guinea pig brains seven hours after exposure to $1.25 \times LD_{50}$ soman show considerable brain damage compared to controls. Initial MRI studies indicate that the spin-to-spin relaxation time (T2) value of the tissue in various regions of the brain increased in the first 6-7 hours following exposure of the guinea pigs to $1.25 \times LD_{50}$ soman. This increase in T2-value remained elevated in most regions and was easily seen as changes in T2-signal intensity following soman exposure. As a result of the prolonged T2, there was a significant increase in T2-weighted signal intensity in various brain regions at 6-7 hours following exposure to $1.25 \times LD_{50}$ soman. The sustained significant signal increase at 6-7 hours following soman exposure suggests a combination of cellular and vasogenic edema. The soman-induced enhancement of T2 values were not observed in the brains of galantamine-treated, soman-challenged guinea pigs that showed no evidence of cellular or vasogenic edema. (FIG. 7).

Figure 8:
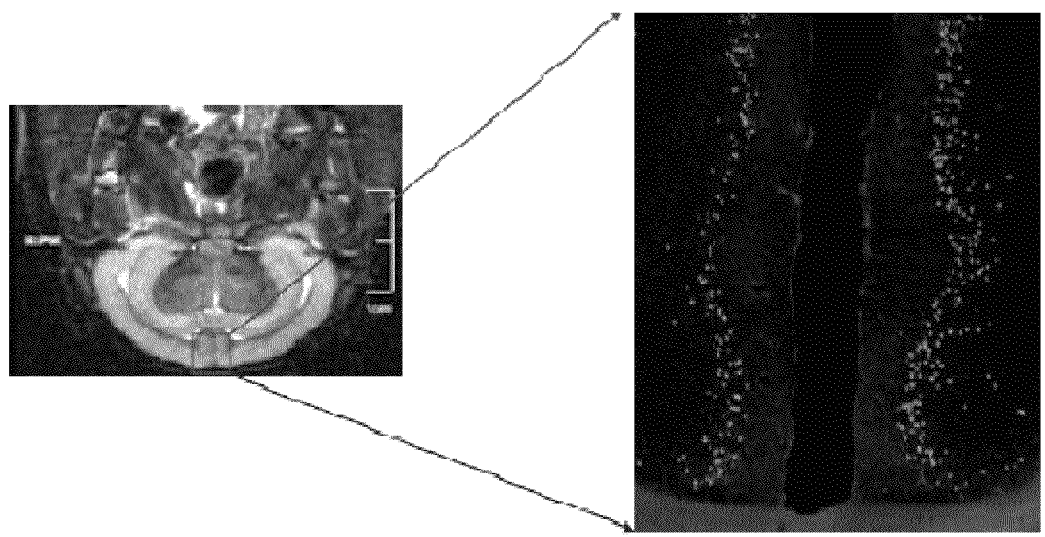
FIG. 8 Histological confirmation of brain damage caused by acute exposure to $1.25 \times LD_{50}$ using a Fluoro-Jade B stain.

Autopsy samples stained with neurogranin mRNA or Fluoro-Jade-B confirmed the MRI observations (FIG. 8). The loss of neurons in the brains of soman-challenged guinea pigs is evidenced by the loss of neurogranin mRNA hybridization and by the appearance of large numbers of Fluoro Jade-B-positive neurons. Neurogranin mRNA is a transcript selectively expressed by neurons in the brain. As neurons are lost, the signal for neurogranin mRNA decreases. By contrast, pretreatment with 8 mg/kg galantamine 30 minutes before soman exposure prevented soman-induced loss of neurons. In situ hybridization showed that the level of transcripts for neurogranin in the brain of galantamine-treated, soman-challenged animals is similar to that observed in the brains of control (saline-injected) animals. In addition, no Fluoro Jade-B-positive neurons were detected in the brains of galantamine-treated, soman-challenged animals.

Voxel-based morphometric contrast maps between images of guinea pigs treated with galantamine (8 mg/kg, i. m.) and 30 minutes later exposed to 1.25×LD50 soman showed that galantamine effectively prevented brain damage. (FIG. 9)

Mechanisms Underlying the Effectiveness and Safety of the Galantamine-Based Therapy Against OP Intoxication The exact mechanisms that account for the superiority of galantamine as a countermeasure against OP poisoning are yet to be fully elucidated. However, without being bound by theory, it can be postulated that the effectiveness of galantamine is related both to the higher potency with which it selectively inhibits AChE compared with BuChE (Thomsen, T. & Kewitz, H. (1990) *Life Sci.* 46, 1553-1558), an action that should help preserve the scavenger capacity of plasma BuChE for OPs, and to the protection of brain AChE from OP-induced irreversible inhibition. Our discovery that galantamine was essential to counteract soman-induced neurodegeneration in the brain supports the notion that AChE-related and/or -unrelated actions of this drug in the central nervous system contribute to its effectiveness. Neuronal loss in the brains of OP-intoxicated animals correlates to some extent with the intensity and duration of OP-triggered seizures. Yet, neurodegeneration and consequent cognitive impairment induced by OPs can be significantly reduced by therapeutic interventions that, although unable to suppress OP-triggered seizures, effectively decrease glutamate excitotoxicity (Filliat, P., et al. (1999) Neurotoxicology 20, 535-549). The ability of the galantamine-based therapy to prevent OP-induced convulsions at the doses we report, and the well-reported neuroprotective effects of galantamine against different insults may be important determinants of the antidotal effectiveness. (Pereira, E. F. R., et al. (2002) J. Neurobiol. 53, 479-500; Arias, E., (2004) Neuropharmacology 46, 103-114; Kihara, T., et al. (2004) Biochem. Biophys. Res. Commun. 325, 976-982; Nakamizo, T., et al. (2005) Biochem. Biophys. Res. Commun. 330, 1285-1289; and Capsoni, S., et al. (2002) Proc. Natl. Acad. Sci. USA 99, 12432-12437). Because no cognitive impairment has been detected in soman-challenged animals when neuronal loss in their brains remains below a certain threshold (Filliat supra), galantamine can be used therapeutically to maintain normal cognitive performance in OP-exposed subjects.

Based on this evidence, an embodiment is directed to a method of treating or preventing the loss of cognitive function or neuronal degeneration in an animal diagnosed as having organophosphorus poisoning, by administering a therapeutically effective amount of galantamine or a salt thereof, or a biologically active analog, derivative, fragment or variant thereof. In a preferred embodiment, galantamine is administered in an amount of from about 3 to about 10 mg, preferably about 6-10 mg, up to three times per day as long as symptoms of OP poisoning persist. In another preferred embodiment, galantamine is further administered up to three times per day after symptoms of OP poisoning have disappeared at a slightly lower does of about 3-6 mg, for extended periods of time up to about a month after symptoms disappear. This time period can be lengthened at the physician's discretion.

Pharmacokinetics of Galantamine

To help establish the clinical relevance of the doses of galantamine needed to counteract OP poisoning, plasma and brain concentrations of the drug were determined by HPLC at various times after treatment of guinea pigs with 8 mg/kg galantamine. This dose was selected because, (i) in association with atropine, it afforded full protection against OP-induced toxicity and lethality, and (ii) it was half of the minimum dose at which galantamine triggered mild side effects. In guinea pigs, as in humans (Bickel, U., et al. (1991) Clin. Pharmacol. Ther. 50, 420-428), plasma levels of galantamine declined with first-order kinetics. After an i.m. injection of 8 mg/kg galantamine, plasma and brain levels of the drug peaked between 5 and 30 minutes and decayed with half-times of 71.7±14.4 minutes and 57.8±4.31 min, respectively (FIGS. 11 A and B). As shown in FIG. 3A, full protection against acute toxicity was achieved when 8 mg/kg galantamine was administered to guinea pigs up to 1 hour before 1.5×$LD_{50}$ soman, a time when plasma and brain levels of the drug were 0.90±0.01 µg/ml and 0.80±0.04 µg/g, respectively (FIGS. 11A and B). Based on galantamine's molecular weight of 287.4, these findings suggest that the minimal plasma concentration of galantamine needed to prevent OP toxicity and lethality is about 2.8 µM. Doses of galantamine recommended for treatment of patients with Alzheimer's disease are between 8 and 24 mg/day (Corey-Bloom supra). Peak plasma concentrations of 0.2-3 µM have been detected in healthy human subjects treated orally or s.c. with a single dose of 10 mg of galantamine (Bickel supra; and Mihailova, D, (1989) Pharmacology 39, 50-58). Thus, doses of galantamine needed to prevent OP toxicity can be determined as those doses that generate peak plasma concentrations similar to those achieved with doses clinically used to treat Alzheimer's disease.

The efficacy of long-term OP treatment, for example daily treatment of soldiers or civilians at risk of a terrorist attack, or agricultural workers repeatedly exposed to sublethal doses of OP, can be monitored by taking blood samples to measure the plasma levels of galantamine. The therapeutic dose and frequency of administration should be adjusted to maintain plasma galantamine levels at about 2 to about 3 µM. This amount may vary once actual human data is obtained after treatment with galantamine after or before exposure to various amounts of various OPs.

In agreement with the concept that galantamine-induced AChE inhibition is reversible, the degree of AChE inhibition in brain and blood from galantamine-treated guinea pigs decreased as the galantamine levels declined in both compartments. Inhibition of AChE became negligible at 6 hours after the treatment (FIG. 11C), when plasma and brain levels of the drug were less than 0.1 µg/ml and 0.1 µg/g, respectively (FIGS. 11A and B). Maximal inhibition of blood AChE activity was about 70% (FIG. 11C), observed at 30 minutes after the treatment when the plasma levels of galantamine had peaked. The effectiveness of galantamine in patients with Alzheimer's disease has been correlated with 40-70% inhibition of AChE in blood (Jann, M. W., et al. (2002) Clin. Pharmacokinet. 41, 719-739).

Maximal AChE inhibition in the brains of galantamine-treated animals was significantly different from that observed in their blood (FIG. 11C). Measured peak concentrations of galantamine were 1.6±0.13 µg/ml in the plasma and 1.38±0.11 µg/g in the brain. These concentrations resulted in about 70% and 25% inhibition of AChE in the blood and brain, respectively. Measured peak levels of galantamine in the plasma correspond to 5.6±0.5 µM. Considering 80% of the brain weight as water, measured peak levels of galantamine in brain tissue would correspond to 3.8±0.3 µM. Based on the concentration-response relationships obtained for galantamine-induced inhibition of guinea pig blood and brain AChE in vitro (FIG. 11D), it is estimated that 5.6 µM galantamine would inhibit blood acetylcholinesterase activity by 68%, and 3.8 µM galantamine would inhibit brain AChE activity by 25%. In vitro, galantamine inhibited guinea pig blood and brain AChE with EC50 values of 1.8±0.38 µM and 16.9±9.8 µM, respectively (mean±SEM; FIG. 11D). In humans, blood AChE activity is also 10-fold more sensitive to inhibition by galantamine than is brain AChE activity (Thomsen, T., et al. (1991) Eur. J. Clin. Chem. Clin. Biochem. 29, 487-492).

Inhibition of brain AChE by about 60-70% has been shown to trigger severe incapacitating effects, including seizures (Tondulli, L. S., et al. (1999) J. Neurosci. Res. 58, 464-473). Maximal degrees of inhibition of AChE activities observed in guinea pigs treated with doses of galantamine that effectively counteracted OP intoxication (about 8 mg) were about 70% in blood and but only about 25% in brain. All other centrally acting acetylcholinesterase inhibitors studied to date, including huperzine, acutely prevent OP toxicity when used at doses that decrease both blood and brain AChE activity by about 70% (Deshpande, S. S., et al. (1986) Fundam. Appl. Toxicol. 6, 566-577; Grunwald, J., et al. (1994) Life Sci. 54, 991-997; Fricke, R. F., et al. (1994) Drug Chem. Toxicol. 17, 15-34; and Lallement, G., et al. (2002) Neurotoxicology 23, 1-5.)

Therefore, a high degree of reversible and selective AChE inhibition in the blood appears to counteract the peripheral toxic effects of OPs acutely. A low degree of reversible inhibition of brain AChE may be sufficient to protect a significant pool of AChE from OP-induced irreversible inhibition, thus limiting the occurrence of untoward side effects of centrally acting reversible AChE inhibitors. Our discovery that galantamine at low, non-toxic doses protects against OP poisoning, whether caused by sublethal or highly lethal doses of OP, was unexpected in view of the literature on anticholinesterase therapy using other inhibitors.

Mild nausea is a common side effect of galantamine; it usually occurs when galantamine is first administered, but this passes and does not reoccur. If the subject is a woman, there is a very slight risk of galantamine causing a spontaneous abortion (less than 0.1%). Another contraindication for administering galantamine long term is cardiac hypertension which can be temporarily increased by galantamine. With all of these situations, however, the risk is typically outweighed by the benefit of treating or preventing organophosphorus poisoning.

Pharmaceutical Compositions

Certain galantamine analogs and derivatives that can be used in the present invention are described inter alia in Davis et al., U.S. Pat. No. 6,150,354, Davis et al., U.S. Pat. No. 6,319,919, and Davis et al., U.S. Pat. No. 6,670,356. Certain controlled release preparations of galantamine are described in Gore et al., U.S. Application No. US 2007/0092568. Amounts of galantamine that are sufficient to treat or prevent OP poisoning can be determined in accordance with dosage range-finding techniques such as are known in the art (see e.g., E. Albuquerque et al., Aug. 29, 2006, vol. 103, no. 35, pgs 13220-13225 and W. H. Carter et al., (1985), Fundam. Appl. Toxicol. 5, S232-S241, incorporated herein by reference). Based on the experiments described herein, the preferred dose of galantamine should be from about 3 to about 12 mg, administered up to 3 times per day for up to a month after exposure, depending on the organophosphorus poisoning exposure. In other embodiments, long term galantamine therapy for low dose, recurrent OP exposure such as for agricultural workers typically involves a lower does of about 3-6 mg, possible over a period of many months or even years. However, higher doses of galantamine up to 24 mg could be needed under certain circumstances, for example, for exposure to very low doses of OP pesticides.

Galantamine for treating organophosphorus poisoning can be administered by any suitable means, including transdermal, parenteral, rectal, and nasal administration. Parenteral infusions include intramuscular, intravenous, intraarterial, intraperitoneal, or subcutaneous administration. In a preferred embodiment, galantamine is administered by injection, most preferably by intramuscular injection, or by oral administration. Oral administration of galantamine is preferable for treating individuals exposed to sub-lethal doses of OP, such as agricultural workers or workers making pesticides or for long term administration. Atropine can be similarly administered, except that intravenous atropine should be done by a professional as it is potentially dangerous. In a preferred embodiment, galantamine and atropine are formulated into a single composition, preferably in an amount of from about 3-12 mg galantamine and 1-12 mg atropine. These amounts may vary when actual human data is obtained.

Therapeutically effective amounts of galantamine can be formulated into various pharmaceutical compositions known in the art, including liquid solutions or suspensions, and solid forms including those described in more detail in U.S. Pat. App. Serial Nos.: US 2007/0092568 A1, US 2004/0097484, WO 2005/065661, WO 2005/048979 and WO 2005/065661; incorporated herein by reference.

The term "active ingredient", as used below, refers to galantamine and its pharmaceutically acceptable and therapeutically active salts, analogs, derivatives, fragments, and variants including esters, amides, prodrugs, metabolites, enantiomers, polymorphs, analogs, etc. that induce a desired pharmacological or physiological effect. Terms like "active", "active agent", "active substance", "active pharmaceutical substance", "pharmacologically active agent", "drug" and "drug substance" may be used synonymously for "active ingredient".

Galantamine can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Pharmaceutical compositions of galantamine suitable for administration to a subject in need of prophylaxis or therapy for organophosphorus poisoning may contain, for example, such normally employed additives as binders, fillers, carriers, preservatives, stabilizing agents, emulsifiers, buffers, disintegrants, colorants, anti-oxidants, sweeteners, film-forming agents and excipients known in the art that are compatible and physiologically tolerable. Topical formulations include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016. Liposomal delivery methods may also be employed (See, e.g., U.S. Pat. Nos. 5,851,548 and 5,711,964).

Formulations of galantamine may contain more than one active compound such as atropine or other muscarinic receptor antagonist, as necessary for the particular indication being treated, preferably those with complementary activities that do not adversely affect each other. Such molecules are suitably present in combination in amounts that are effective for the purpose intended.

Administration forms releasing active substances in a controlled or sustained manner are already known in the art, including the controlled release preparations of galantamine described in Gore et al., U.S. Application No. US 2007/0092568, incorporated herein by reference.

The appropriate dosage will vary according to the type, amount and duration of OP exposure as discussed above and whether the drug is administered before or after exposure, to treat or prevent OP. It may also vary according to the patient's clinical history and response to the drugs and the discretion of the attending physician. Galantamine can be administered to the patient once or multiple times on the same day, or over a period of many days, weeks, months and, in some cases of continuous risk of low dose exposure, even years. In the case of agricultural workers exposed to sublethal doses of OP on a reoccurring basis, administration may be over the entire time of exposure.

Galantamine used in the present inventions can be in the form of the base or a pharmaceutically acceptable salt, or combinations of base and one or more salts, or combinations of one or more salts. Pharmaceutically acceptable salts of galantamine include but are not limited to the hydrochloride, hydrobromide and the like. Galantamine hydrobromide has been used therapeutically in the range of about 2 mg to 60 mg. For the purpose of this invention, galantamine is more preferably administered in an amount of from about 3 to about 12 mg per dosing unit; amounts up to about 24 mg could be used, for example after exposure to very low amounts of certain OPs.

Galantamine formulated for immediate release or extended release includes particles prepared as powders, granules, pellets, beads and the like using manufacturing processes such as direct blending, dry granulation, wet granulation, pelletization techniques such as but not limited to extrusion-spheronization, dry powder or solution or dispersion layering of galantamine onto inert beads or pellets or particles using conventional coating techniques or fluid bed coating techniques.

EXAMPLES

Example 1

Materials and Methods

Animal Care and Treatments.

Male albino guinea pigs [Crl(HA)Br; Charles River Laboratories, Wilmington, Mass.] weighing 350-420 g (5-6 weeks old) were used. Galantamine, pyridostigmine, or huperzine were injected in one hindlimb, and atropine was injected in the other. The nerve agents, diluted in sterile saline, and paraoxon, diluted in DMSO, were injected s.c. between the shoulder blades of the animals. All injections (about 0.5 ml/kg) were performed by using disposable tuberculin syringes with 25- to 26-gauge needles. Handling and disposal of nerve agents were according to the rules set forth by the U.S. Army. All conditions for animal maintenance conformed to the regulations of the Association for Assessment and Accreditation of Laboratory Animal Care, complied with the standards of the Animal Welfare Act, and adhered to the principles of the 1996 Guide for the Care and Use of Laboratory Animals (Institute of Laboratory Animal Resources (1996) Guide for the Care and Use of Laboratory Animals (National Academy Press, Washington, D.C.)). Atropine sulfate, pyridostigmine bromide, (plus or minus)-huperzine A, and paraoxon were purchased from Sigma-Aldrich (St. Louis, Mo.). Soman and sarin were obtained from the U.S. Army Medical Research and Development Command (Fort Detrick, Md.). Galantamine HBr was a generous gift from Alfred Maelicke (Galantos, Mainz, Germany).

Histopathological Analyses.

Guinea pigs were anesthetized at appropriate times after their treatments and transcardially perfused with 0.9% saline (70 ml/min) until blood was cleared and subsequently perfused with 10% formalin. Their brains were then removed, placed in 10% formalin for no longer than 48 h, dehydrated, and embedded in paraffin. Sections 5 micrometers thick were cut and then dried in an incubator at 37° C. for 12 hours before they were stained with FJ-B (Schmued, L. C. & Hopkins, K. J. (2000) Brain Res. 874, 123-130.)

After it was mounted, the tissue was examined under an epifluorescence microscope with blue (450-490 nm) excitation light and a filter for fluorescein isothiocyanate. Photomicrographs were taken with a digital microscope camera (AxioCam; Zeiss, Jena, Germany).

Analysis of Galantamine Concentrations in the Brain and Plasma of Guinea Pigs.

At various times after treatment with galantamine (8 mg/kg, i.m.), animals were anesthetized with $CO_2$. Blood (5-10 ml) was collected by cardiopuncture with a plastic heparinized system and kept in dry ice. Immediately after cardiopuncture, the animals were exsanguinated by carotid artery transection. Their brains were removed, superfused with 0.9% saline, and snap frozen in liquid nitrogen. Frozen blood samples and brains were kept at about 80° C. until further processing. Brain and plasma levels of galantamine were measured by using a modified HPLC method (Claessens, H. A., van Thiel, M., Westra, P. & Soeterboek, A. M. (1983) J. Chromatogr. 275, 345-353).

Radiometric Enzymatic Assay.

Pulverized brain tissue was mixed with buffer containing antiproteases (0.5 unit/ml aprotinin, 30 µg/ml leupeptin, 1 mg/ml bacitracin, 2 mM benzamidine, and 5 mM N-ethylmaleimide) and sonicated for 20 seconds on ice. Aliquots of the resulting suspensions and of blood samples were used for determination of protein concentration (micro BCA protein assay; Pierce, Rockford, Ill.). Measurements of acetylcholinesterase activity were performed in the presence of the BuChE inhibitor tetraisopropyl pyrophosphoramide (1 mM) with a modified two-phase radiometric assay (Johnson, C. D. & Russell, R. L. (1975) Anal. Biochem. 64, 229-238) using 20 µM [3H]acetylcholine iodide [specific activity, 76 Ci/mmol (1 Ci=37 GBq); PerkinElmer Life Sciences, Boston, Mass.], which produced about 200,000 cpm when totally hydrolyzed by eel acetylcholinesterase (2 units). These references are incorporated in their entirety as if fully set forth herein, except where terminology not consistent with the definitions herein.

Behavioral Assays.

Locomotor activity and stereotypy of guinea pigs were analyzed in an open-field arena equipped with infrared sensors (AccuScan Instruments, Columbus, Ohio), as described by June et al. (June, H. L., et al., (1995) J. Pharmacol. Exp. Ther. 274, 1105-1112). Counts obtained from the total number of interruptions of the infrared beams were automatically compiled every 5 minutes and processed for measures of total distance traveled and stereotypy.

Example 2

Pre-Exposure Administration of Donepezil, Rivastigmine and (±) Huperzine-A

Figure 12:
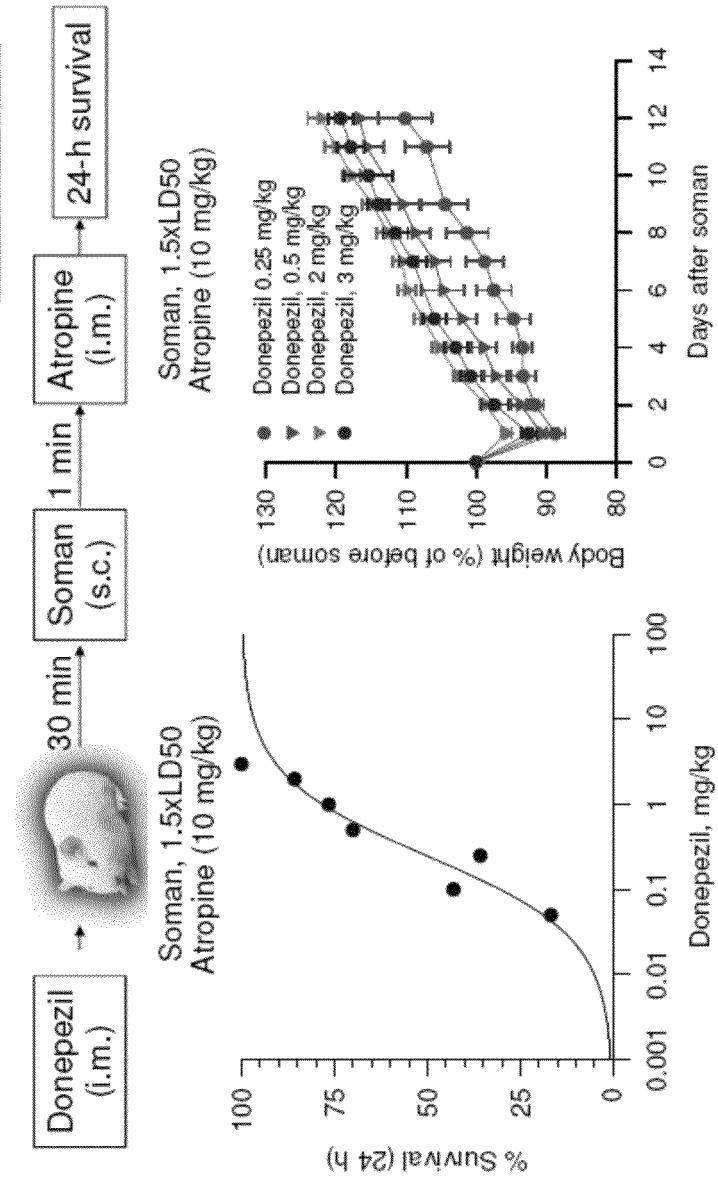
FIG. 12 Effectiveness of donepezil administered 30 minutes before exposure to $1.5 \times LD_{50}$ soman.
Figure 13:
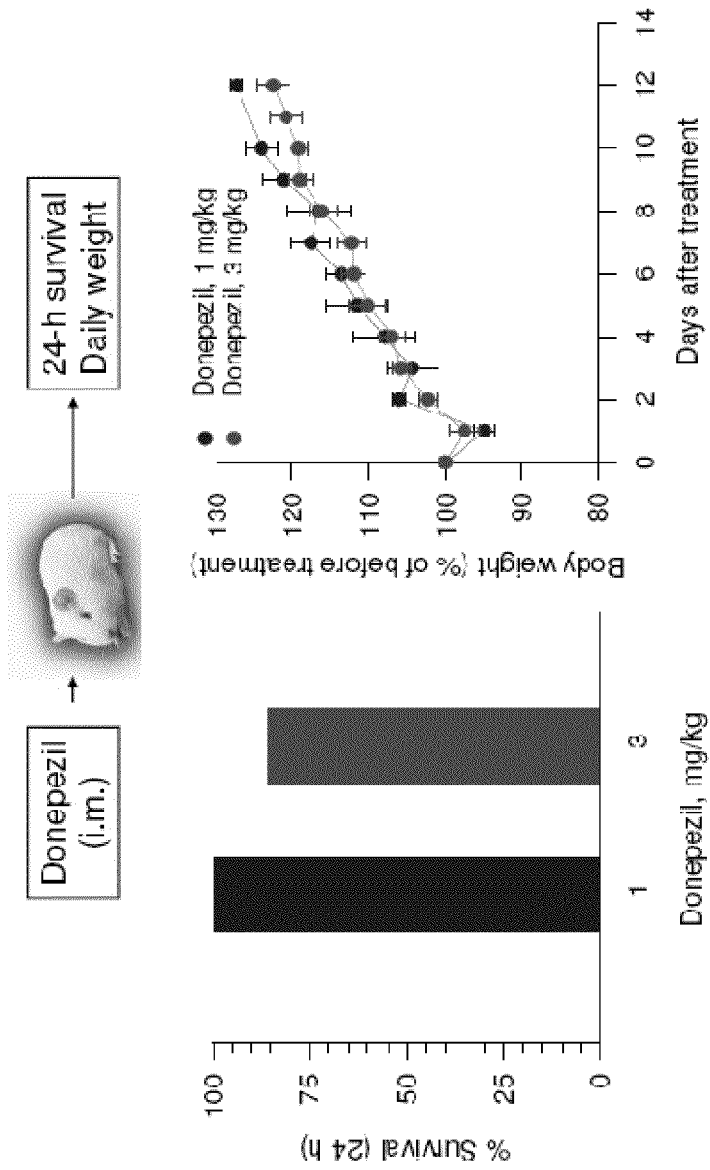
FIG. 13 Toxicity of donepezil.

Donepezil, rivastigmine and (±)Huperzine-A are reversible inhibitors of both central and peripheral AChE. We tested these drugs as potential antidotes for OP intoxication using a $1.5 \times LD_{50}$ soman challenge. Male guinea pigs (35-40-days old) received an i.m. injection of a given dose of one of the test drugs, followed 30 minutes later by an s.c. challenge with $1.5 \times LD_{50}$ soman (42 µg/kg), and 1 minute later by an i.m. injection of atropine sulfate (10 mg/kg). Each experimental group consisted of 8-10 guinea pigs. Full protection against the lethality of $1.5 \times LD_{50}$ soman was achieved when the animals received 3 mg/kg donepezil 30 minutes before the OP challenge, provided that atropine (10 mg/kg, im) was administered 1 minute after the nerve agent. FIG. 12. Importantly, we discovered that the therapeutic doses of donepezil are by themselves toxic. The data in FIG. 13 showed that 3 mg/kg i.m. donepezil by itself decreased the survival of the animals by 15% at 24 hour post-administration. However, even animals given 1 mg/kg donepezil showed clear signs of cholinergic intoxication, including hyperactivity and difficulty breathing. Thus, in the therapeutic regimen of donepezil/ atropine for treatment of OP intoxication, atropine helps to reduce the cholinergic toxicity of both donepezil and soman.

Figure 14:
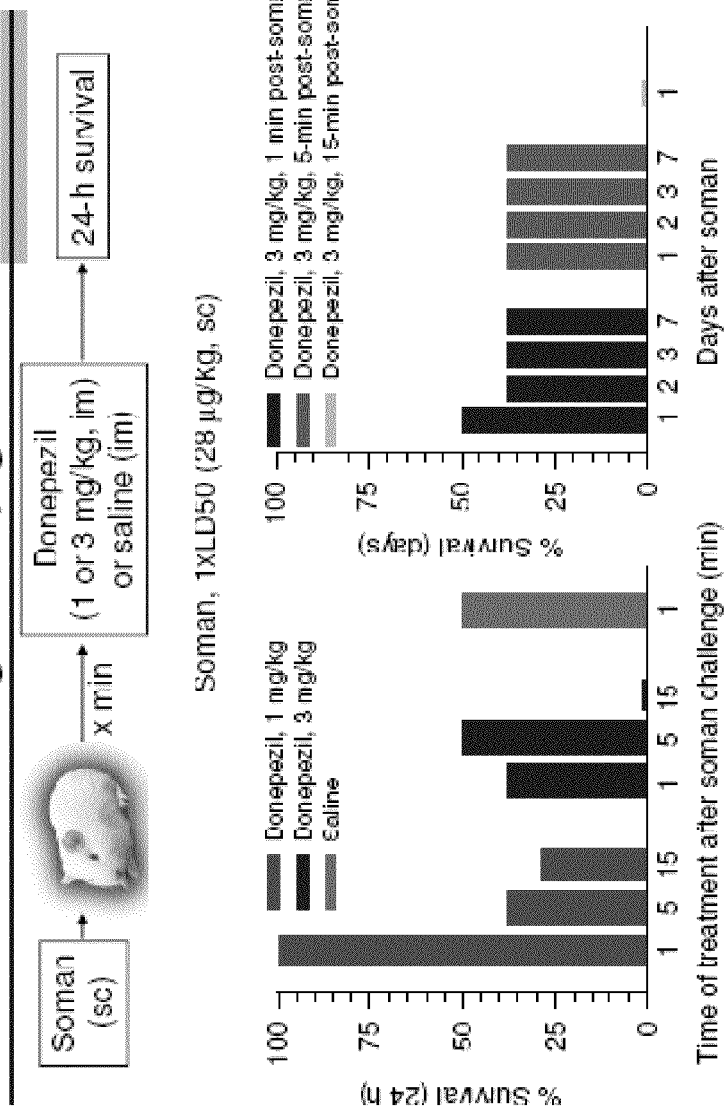
FIG. 14 Effectiveness of donepezil administered after exposure to $1.0 \times LD_{50}$ soman.

FIG. 14 shows the effectiveness of donepezil as a post-treatment therapy given 1-15 minutes after exposure to 1.0 $LD_{50}$ soman. All animals treated with 1 mg/kg donepezil survived the exposure to $1 \times LD_{50}$ soman, though they presented signs of cholinergic intoxication, including chewing, tremors, and hyperexcitability. In contrast, only 35% of the guinea pigs treated with 3 mg/kg donepezil survived the exposure to $1 \times LD_{50}$ soman. The lower effectiveness of the higher dose of donepezil can be accounted for by the significant level of inhibition of brain AChE achieved in animals that are exposed to soman and subsequently exposed to such dose of donepezil.

Figure 15:
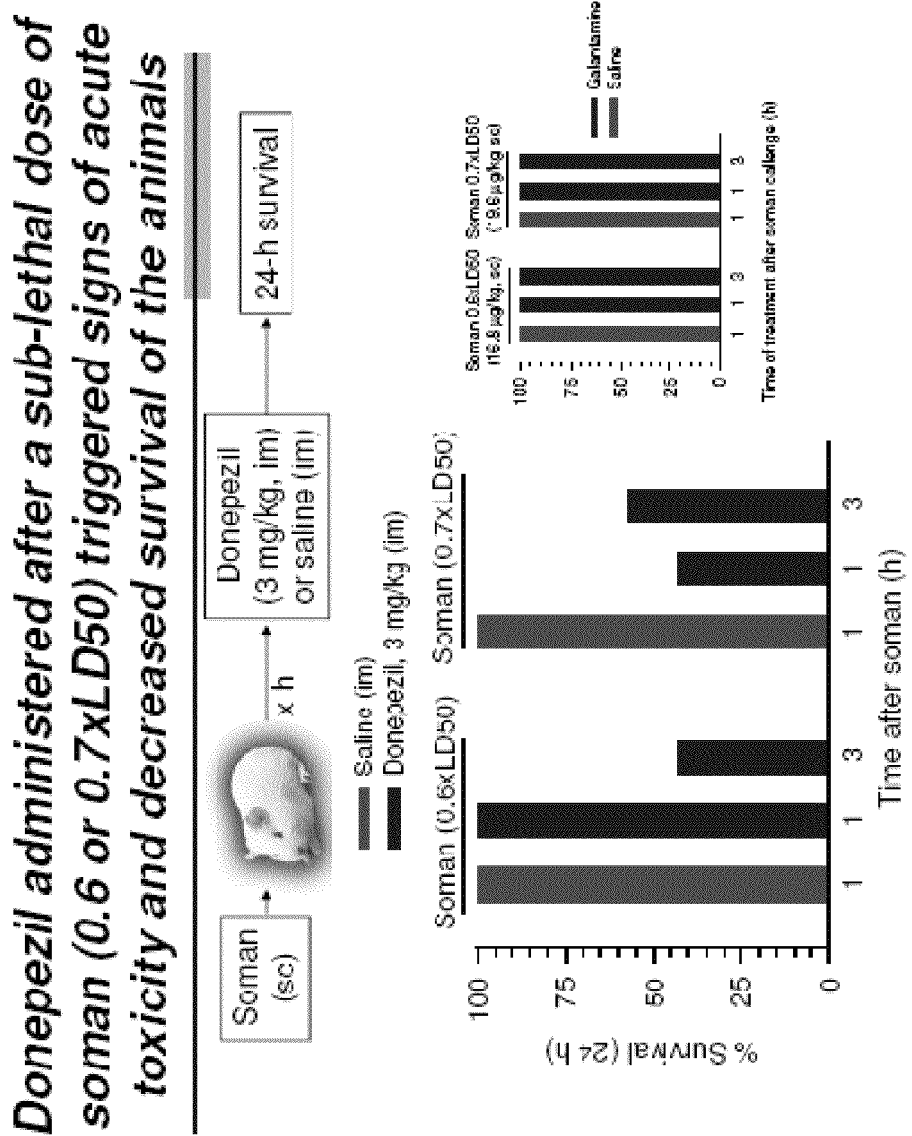
FIG. 15 Effectiveness of donepezil administered after exposure to sublethal doses of soman.

FIG. 15 shows that administration of donepezil 1-3 hours after sublethal doses of soman ($0.6$-$0.7 \times LD_{50}$) decreases the survival of the guinea pigs. Donepezil at 1 mg/kg did not alter the survival of the animals if given one hour after exposure to sublethal doses of soman. However, if donepezil treatment was delayed until 3 hours post-exposure, the 24 hour survival of the soman-exposed guinea pigs dropped to 40%. The reduction in the survival of the animals could be accounted for by the additive effects of soman and donepezil on AChE inhibition, particularly in the brain. After exposure to $0.7 \times LD_{50}$ soman, 3 mg/kg donepezil decreased to 40% the survival of the animals if given 1 hour after the exposure. Administering 3 mg/kg donepezil at 3 hours after the exposure to $0.7 \times LD_{50}$ soman decreased to 60% the survival of the animals. The slightly higher survival observed upon increasing the interval between the injections of $0.7 \times LD_{50}$ soman and 3 mg/kg donepezil may be due to a better competition between soman and higher concentrations of donepezil at AChE.

Figure 16:
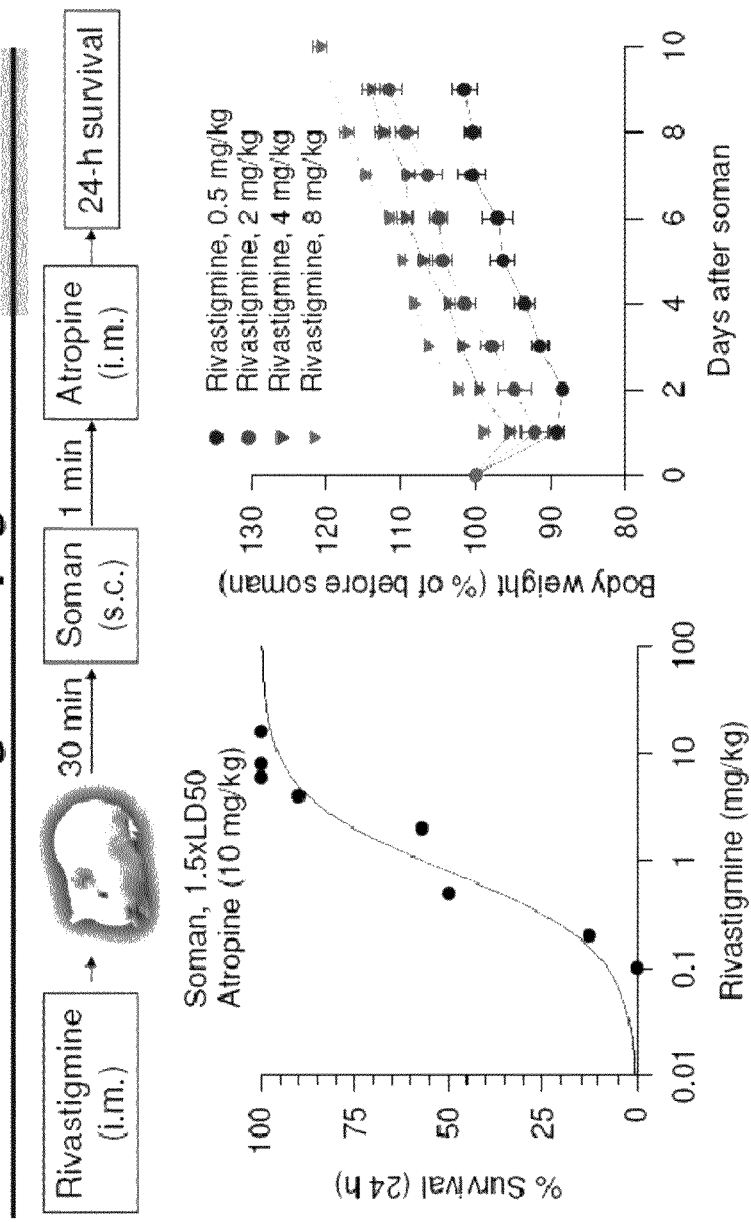
FIG. 16 Effectiveness of rivastigmine administered before exposure to $1.5 \times LD_{50}$ soman.
Figure 17:
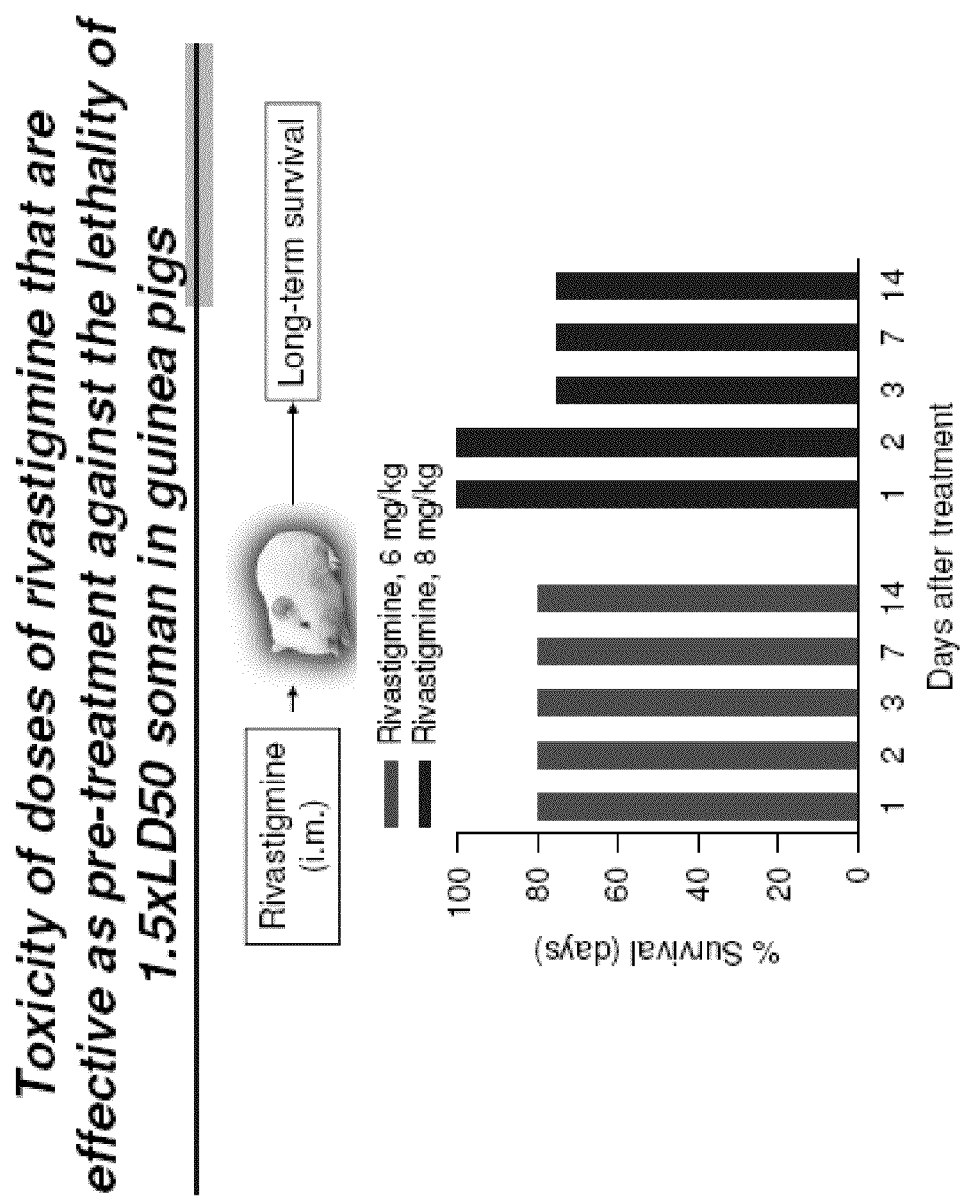
FIG. 17 Toxicity of rivastigmine.

We next looked at treatment with rivastigmine. Each experimental group consisted of 8-10 animals. We observed that full protection was achieved with 6-8 mg/kg rivastigmine given 30 minutes before the $1.5 \times LD_{50}$ OP challenge, when 10 mg/kg atropine was administered to the animals soon after the OP challenge (FIG. 16). The toxicity study showed that 6 mg/kg rivastigmine caused 20% fatality by itself by day one. However, no further increase in fatality rate was seen by 14 days after administration (FIG. 17). It is clear that atropine is necessary to counteract the toxicity of both rivastigmine and soman.

Figure 18:
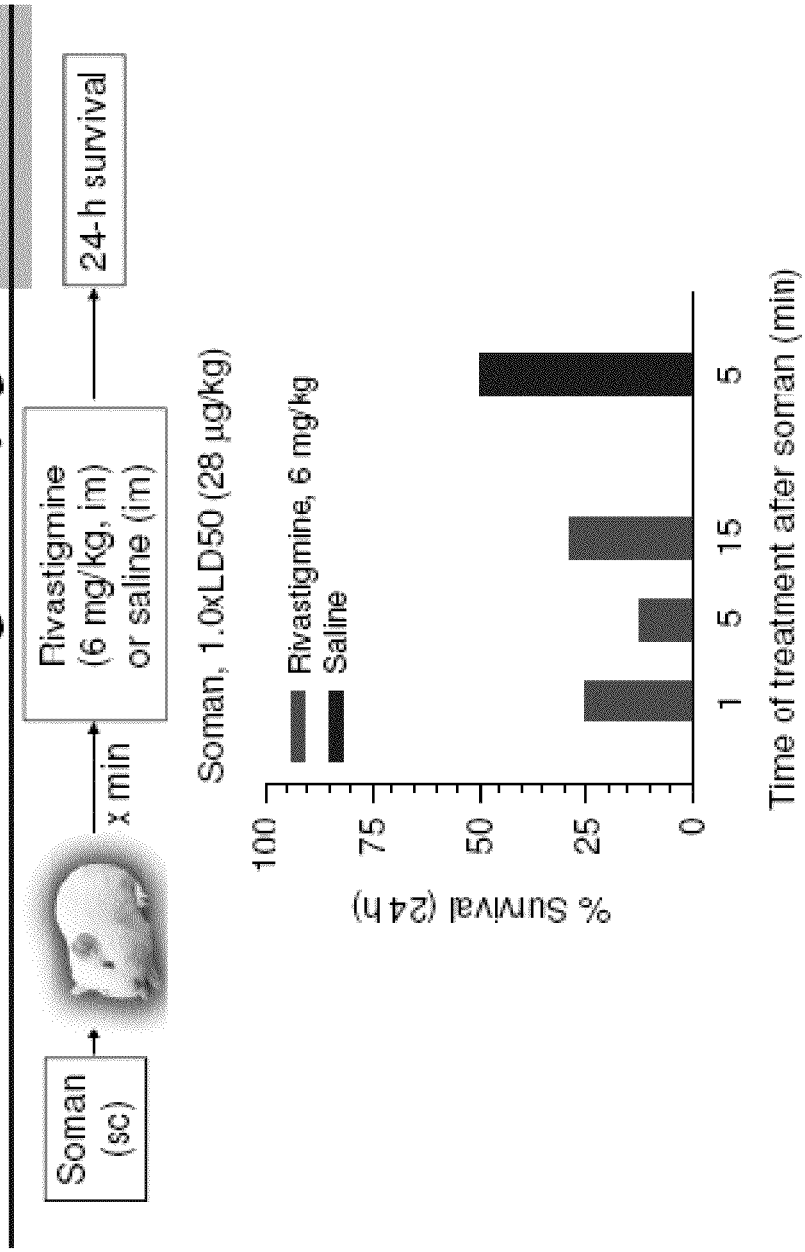
FIG. 18 Effectiveness of rivastigmine administered after exposure to $1.0 \times LD_{50}$ soman.
Figure 19:
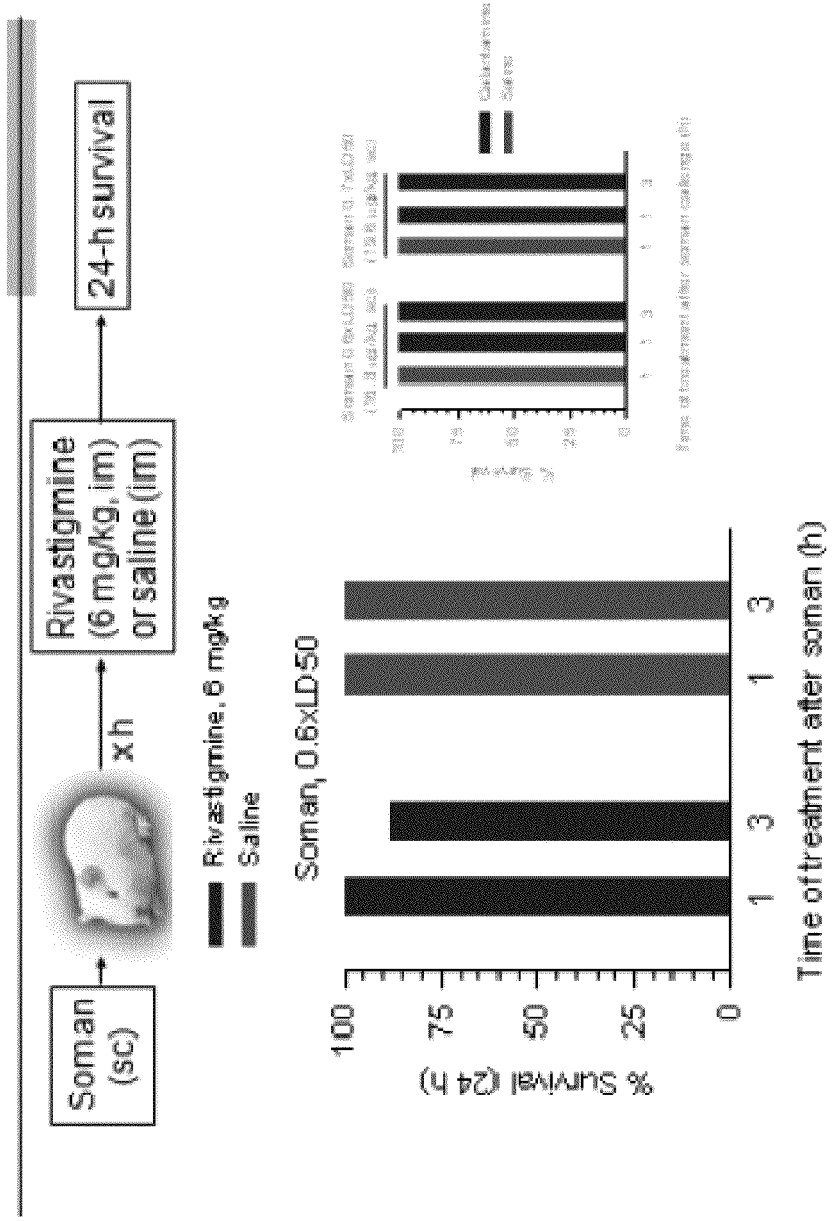
FIG. 19 Toxicity of rivastigmine administered after sublethal doses of soman.

FIG. 18 shows the effectiveness of 6 mg rivastigmine given between 1-15 minutes after exposure to $1.0 \times LD_{50}$. Treatment with 6 mg/kg rivastigmine between 1 and 15 minutes after exposure to 1 $LD_{50}$ soman was less effective than no treatment at all. However, this dose of rivastigmine, when followed with atropine, fully protected guinea pigs challenged with $1 \times LD_{50}$ soman, because, as alluded to above, atropine helped counteract the toxicity of both soman and rivastigmine. Rivastigmine (6 mg/kg) administered 1-3 hours after sublethal amounts of $0.6 \times LD_{50}$ soman did not affect the survival outcome of the animals, which remained at 100% if administered at 1 minute after the challenge. However, rivastigmine decreased to 85% the survival of the animals if administered 3 hours after soman. FIG. 19. The reduced survival of the animals with rivastigmine under these circumstances could be accounted for by the acute toxicity of rivastigmine.

Figure 20:
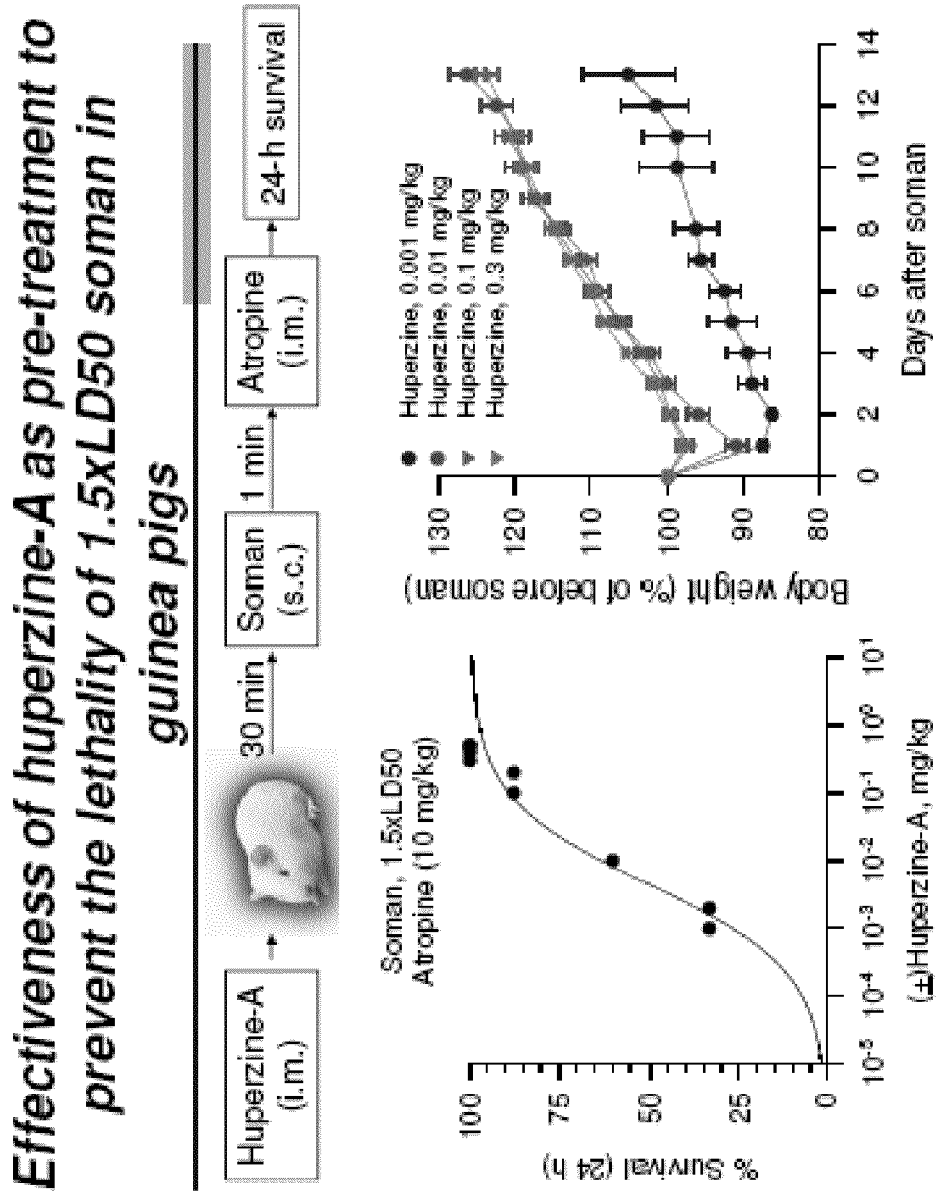
FIG. 20 Effectiveness of huperzine-A administered before exposure to $1.5 \times LD_{50}$ soman.
Figure 21:
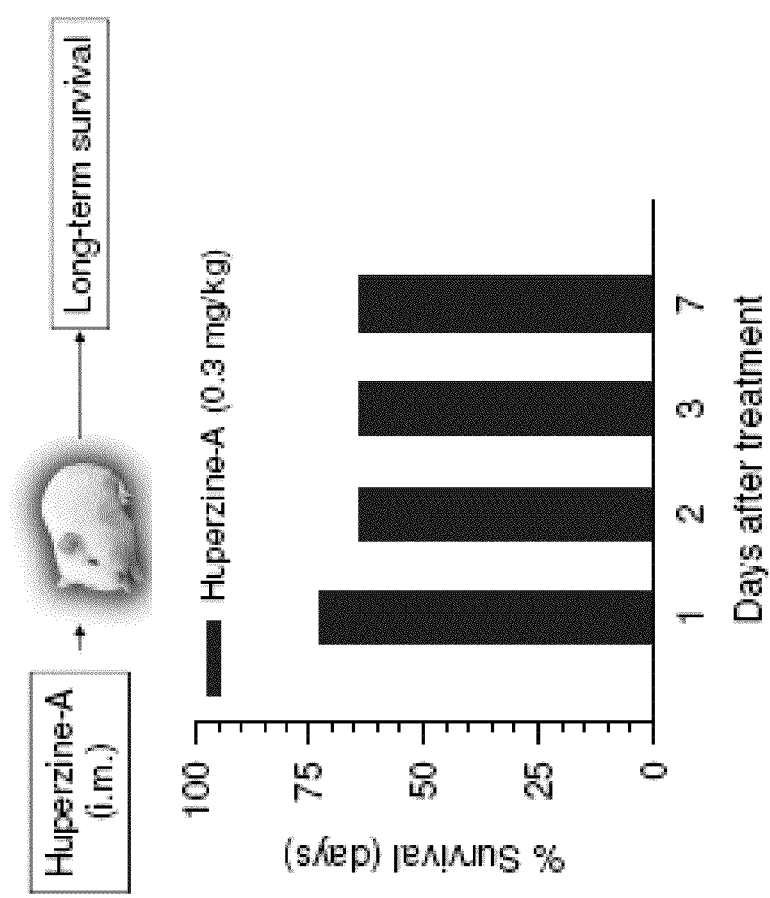
FIG. 21 Toxicity of huperzine-A.
Figure 22:
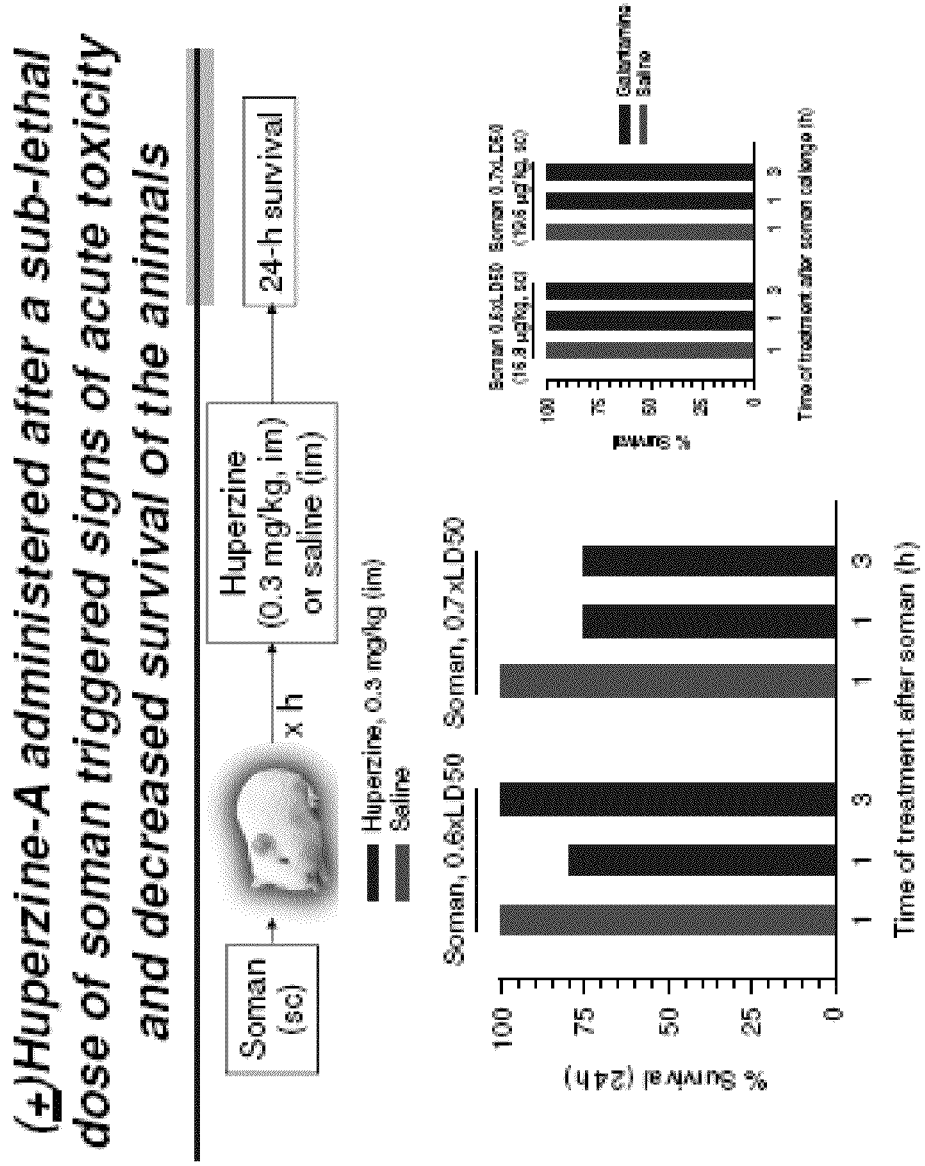
FIG. 22 Toxicity of huperzine-A administered after exposure to sublethal soman.

The results in FIG. 20 show that full protection was achieved with or 0.3-0.5 mg/kg huperzine-A administered 30 minutes before challenge with $1.5 \times LD_{50}$ soman, given that atropine (10 mg/kg, i.m.) was administered soon after soman. However, the toxicity study showed that 0.3 mg/kg caused 30% fatality by itself by day one. By day 2 the fatality leveled off to about 65% at which level it remained through day 7 post-administration. FIG. 21. In the post-treatment regimen, the animals received $1 \times LD_{50}$ soman and 1-15 minutes later received an injection of 0.3 mg huperzine, the dose that afforded full protection in the pre-treatment protocol. No atropine was administered. Treatment with 0.3 mg/kg huperzine between 1 and 15 minutes after exposure to $1 \times LD_{50}$ soman was about 30% at 1 minute, 65% at 5 minutes and 40% at 15 minutes. The differential survival outcome can be explained by the effective competition between huperzine and soman at AChE and the additive effect of both inhibitors.

Figure 23:
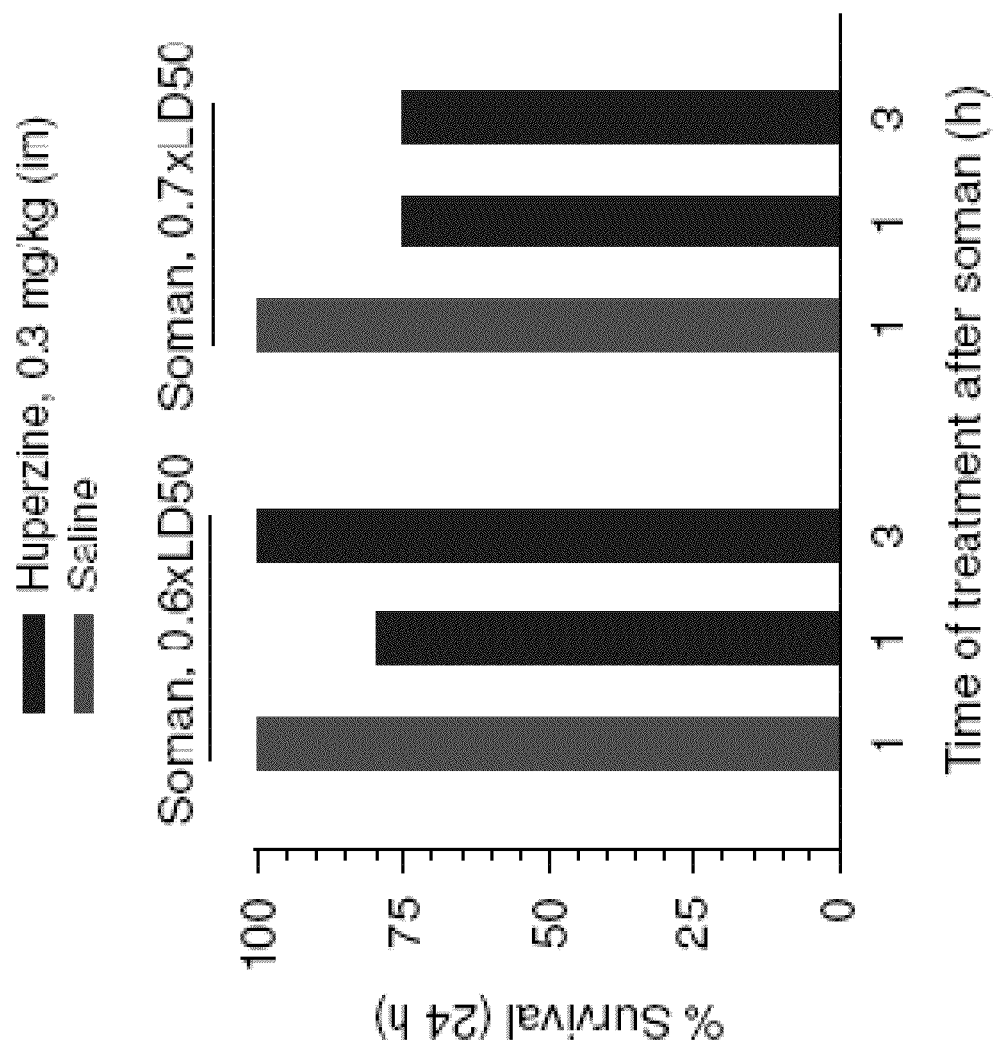
FIG. 23 Effectiveness of huperzine-A administered before exposure to $1.0 \times LD_{50}$ soman.

A dose of 0.3 mg/kg huperzine was tested at 1 hour or 3 hours after challenge of the guinea pigs with $0.6$-$0.7 \times LD_{50}$. The results show that survival was about 80% if huperzine was administered 1 hour after exposure to $0.6 \times LD_{50}$ and $0.7 \times LD_{50}$, and at 3 hours after $0.7 \times LD_{50}$. Survival was about 100% if 0.3 mg/kg huperzine was administered 3 hours after exposure to $0.6 \times LD_{50}$. FIG. 23. As above, the differential survival outcome can be explained by the effective competition between huperzine and soman at AChE and the additive effect of both inhibitors. These results reflect the toxicity of huperzine at these doses.

Example 3

Soman and Sarin Selectively Inhibits RBC Acetylcholinesterase 2-fold More Potently Than Brain Acetylcholinesterase In vitro studies have reported that in humans, as in guinea pigs, brain acetylcholinesterase is less sensitive than RBC acetylcholinesterase to inhibition by galantamine (Thomsen et al., Eur J Clin Chem Clin Biochem 29: 487, 1991). Permeability through the blood-brain-barrier is not the factor that determines the differential inhibition of RBC and brain acetylcholinesterase by galantamine, because this phenomenon is observed in extracts that are exposed in vitro to increasing concentrations of galantamine (Albuquerque et al., PNAS, 2006). The results below show that show that acetylcholinesterase activity in brain and RBC of guinea pigs is also differentially sensitive to the nerve agents soman and sarin. Using the Ellman assay, we have determined that soman and sarin inhibit RBC acetylcholinesterase 2-fold more potently than brain AChE. (Biochem Pharm 7: 88, 1961, which reference is incorporated in its entirety as if fully set forth herein, except where terminology not consistent with the definitions herein.) The exact mechanism underlying the differential sensitivity of brain and blood acetylcholinesterase to inhibition by galantamine or nerve agents remains unclear. It is known that two splice variants of the catalytic subunit of acetylcholinesterase (AChEH and AChET) are present in erythrocyte and neuronal membranes, respectively. These subunits contain identical catalytic domains, but have different C-terminal peptide residues. It is therefore possible that the expression of the different polypeptide catalytic subunits of acetylcholinesterase in these tissues underlie the differences in sensitivity to galantamine inhibition. To test this, the two subunits (human), were expressed in COS7 cells, and acetylcholinesterase activity in cell extracts was measured using a microtiter-adapted Ellman assay. We found that galantamine inhibited acetylcholinesterase activity in a concentration-dependent manner, but the EC50 did not differ significantly in extracts expressing AChEH and AChET ($25 \pm 11$ μM and $23 \pm 7$ μM, respectively). Data not shown. It is therefore likely that the difference in the potency of galantamine to inhibit blood and brain acetylcholinesterase is not explained by the different catalytic polypeptides expressed in these tissues. Furthermore, these results validate the use of a heterologous expression system, as well as the microtiter assay of acetylcholinesterase activity in cell and tissue extracts, to further explore mechanisms underlying the sensitivity of the blood and brain to inhibition by galantamine.

The differential sensitivity of guinea pig red blood cell (RBC) and brain acetylcholinesterase to inhibition by galantamine has been proposed as a mechanism that contributes to its antidotal effectiveness in treating OP poisoning (Albuquerque et al., PNAS, 2006).

While the foregoing specification teaches the principles of the present invention, with examples provided for the purpose of illustration, it will be appreciated by one skilled in the art from reading this disclosure that various changes in form and detail can be made without departing from the true scope of the invention. All references, including publications, patent applications, and patents, cited herein are hereby incorporated by reference to the same extent as if each reference were individually and specifically indicated to be incorporated and were set forth in its entirety herein, except where terminology not consistent with the definitions herein.

What is claimed is:

1. A method for treating or preventing organophosphorus (OP) poisoning in a mammal that is at risk of exposure to OP comprising the steps of:
    administering a therapeutically effective amount of galantamine to the mammal either before or after exposure to OP in an amount of 1.0×LD50 or less and in the absence of administering antimuscarinic to the mammal either before or after exposure to OP.

2. The method of claim 1 wherein the OP exposure is about 0.8×LD50.

3. The method of claim 1 wherein the OP exposure is about 0.7×LD50.

4. The method of claim 1 wherein the OP exposure is about 0.6×LD50.

5. The method of claim 1 wherein the OP exposure is about 0.5×LD50.

6. The method of claim 1 wherein galantamine is galantamine hydro bromide.

7. The method of claim 1 wherein the antimuscarinic is atropine.

8. The method of claim 1 wherein the mammal shows no immediate signs of OP toxicity.

9. The method of claim 1 wherein the mammal is a human and galantamine is administered from one day before to up to three hours after exposure.

10. The method of claim 1 wherein galantamine is administered in an amount of up to about 24 mg.

11. The method of claim 1 wherein the galantamine is administered orally, intranasally, by intramuscular injection, or by subcutaneous injection.

12. The method of claim 1 further comprising administering a therapeutically effective amount of galantamine in the absence of administering anti-convulsants or re-activators of OP-inhibited acetyl cholinesterase.

13. The method of claim 1 further comprising administering a therapeutically effective amount of galantamine to the mammal over an extended period of time.

14. The method of claim 1 wherein the step of administering a therapeutically effective amount of galantamine to the mammal either before or after exposure to OP comprises an initial dose and the method further comprises administering additional doses of a therapeutically effective amount of galantamine to the mammal, which may be the same or different to the initial dose, over an extended period of time.

15. The method of claim 14 wherein galantamine initially is administered up to about 24 hours before or up to about 3 hours after OP exposure and additional doses of galantamine are administered daily for so long as the risk of exposure is present.

16. The method of claim 14 wherein galantamine initially is administered up to about 24 hours before or up to about 3 hours after OP exposure and additional doses of galantamine are administered about 3 times per day for so long as the risk of exposure is present.

17. The method of claim 15 wherein the mammal is a human and the additional doses of galantamine are from about 3 to 10 mg per dose.

18. The method of claim 15 wherein the mammal is a human and the additional doses of galantamine are a maintenance dose of from about 3 to 6 mg per dose.

19. The method of claim 18 wherein the mammal is a human and the maintenance doses are provided for up to about a month after no symptoms of OP poisoning are exhibited.

20. A method for treating organophosphorus (OP) poisoning in a mammal that is at risk of exposure to OP on a recurring basis or preventing OP poisoning in a mammal that has been exposed to OP comprising administering multiple doses of galantamine to the mammal before or after exposure or both before and after exposure to OP in an amount of 0.8×LD50 or less in therapeutically effective amounts for an extended treatment period.

* * * * *